United States Patent [19]

Cheng et al.

[11] Patent Number: 5,646,126

[45] Date of Patent: Jul. 8, 1997

[54] STEROL MODIFIED OLIGONUCLEOTIDE DUPLEXES HAVING ANTICANCER ACTIVITY

[75] Inventors: Yung-chi Cheng, Woodbridge, Conn.; Eugeny A. Lukhtanov, Bothell; Rich B. Meyer, Jr., Woodinville, both of Wash.; Balakrishna S. Pai, New Haven, Conn.; Michael W. Reed, Seattle, Wash.; James H. Zhou, West Haven, Conn.

[73] Assignees: Epoch Pharmaceuticals; Yale University

[21] Appl. No.: 202,927

[22] Filed: Feb. 28, 1994

[51] Int. Cl.[6] .......................... A61K 48/00; C12Q 1/68; C07H 21/02; C07H 21/04
[52] U.S. Cl. ................... 514/44; 435/6; 536/22.1; 536/23.1; 536/24.3; 536/24.5
[58] Field of Search .................. 435/6; 536/22.1, 536/23.1, 24.3, 24.5; 514/44

[56] References Cited

FOREIGN PATENT DOCUMENTS

324474 A1   1/1989   European Pat. Off. .
WO92/07960  5/1992   WIPO .

OTHER PUBLICATIONS

Chu et al, "The stability of different forms of double-stranded decoy DNA in serum and nuclear extracts", Nucleic Acids Res. 20(21):5857–5858 1992.

Gryaznov et al, "Modulation of oligonucleotide duplex and triplex stability via hydrophobic interactions", Nucleic Acids Res. 21(25):5909–5915 1993.

Ma et al, "Design and synthesis of RNA miniduplexes via a synthetic linker approach. 2. Generation of covalently closed, double stranded cyclic HIV–1 TAR RNA analogs with high Tat binding affinity", Nucleic Acids Res. 21(11):2585–2589 1993.

Ma et al, "Design and synthesis of RNA miniduplexes via a synthetic linker approach", Biochemistry 32:1751–1758 1993.

Bielinska et al, "Regulation of gene expression with double-stranded phosphorothioate oligonucleotides", Science 250:997–1000 Nov. 1990.

MacKellar et al, "Synthesis and physical properties of anti–HIV antisense oligonucleotides bearing terminal lipophilic groups", Nucleic Acids Res. 20(13):3411–3417 1992.

Zhou et al, "Discovery of short, 3' cholesterol modified DNA duplexes with unique antittumor cell activity", Cancer Res. 54:5783–5787 Nov. 1994.

Stanfield et al., "Synthesis of protected amino alcohols: a comparative study", J. Org. Chem., 46:4799 (1981).

Gamper, H. B. et al., "Facile preparation and exonuclease stability of 3' modified oligodeoxynucleotides", Nucleic Acids Res., 21, 145–150 (1993).

Reed, M. W. et al., "Arcidine and cholesterol–derivatized solid supports for improved synthesis of 3'–modified oligonucleotides", Bioconjugate Chem., 2, 217–225 (1993).

Atkinson, T. and Michael S., "Solid–phase synthesis of oligodeoxyribonecleotides by the phosphitetriester method", Oligonucleotide Synthesis: A Practical Approach, M. J. Gait, ed., IRL Press, pp. 35–81 (1984).

Primary Examiner—George C. Elliott
Assistant Examiner—Jeffrey Fredman
Attorney, Agent, or Firm—Klein & Szekeres, LLP

[57] ABSTRACT

Oligonucleotides having approximately 8 to 18 nucleotide units and a 3'-tail which includes asteroid structure attached to the 3'-end through the A ring of the steroid skeleton and which form substantially stable duplexes at physiological temperature, have selective cytotoxic activity against certain tumor cell lines.

32 Claims, 15 Drawing Sheets

Figure 1
Formula 2:
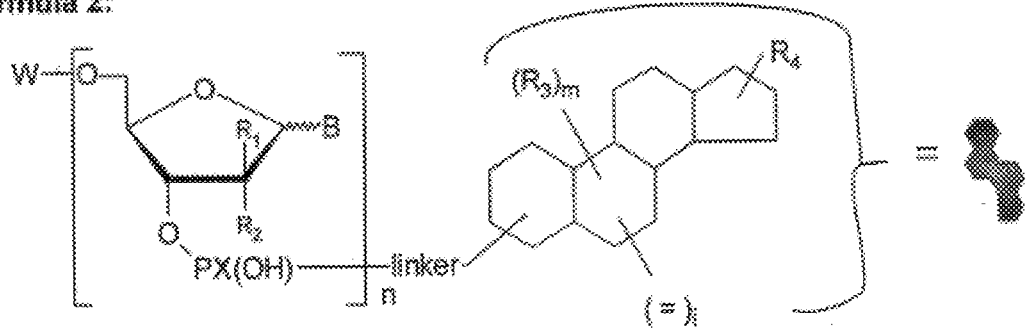
Type 1:
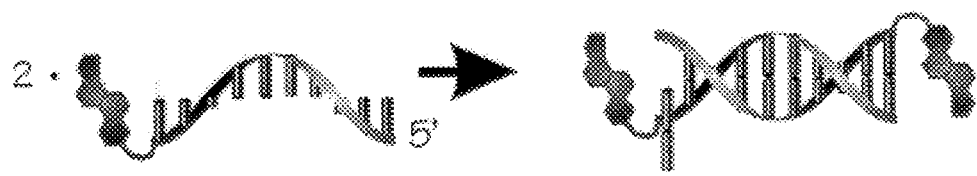
Type 2:
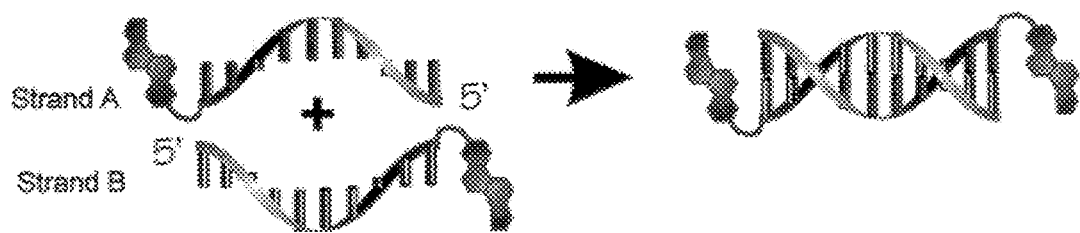
Type 3:
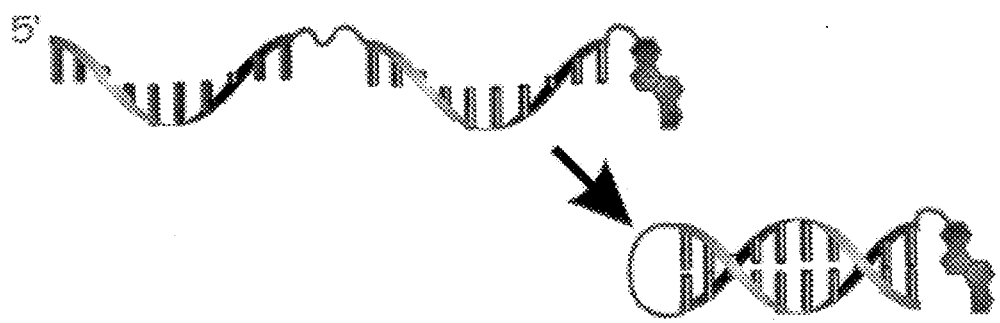

Figure 2.

| Human cell lines | | Results of CMC Assay | |
|---|---|---|---|
| HepG2 | Hepatoma | + | Vacuoles, Vesicles |
| HepG2, 2.2.15 | Hepatoma with HBV | + | Vacuoles, Vesicles |
| LoVo | Colon Carcinoma | + | Vacuoles, Vesicles |
| SW 837 | Colon Carcinoma | + | Vacuoles, Vesicles |
| SW 480 | Colon Carcinoma | + | Vacuoles, Vesicles |
| Caco-2 | Colon Carcinoma | + | Vacuoles, Vesicles |
| HT-29 | Colon Carcinoma | + | Vacuoles, Vesicles |
| KB | Naso-pharyngeal Carcinoma | - | |
| $KB_{MDR}^+$ | Naso-pharyngeal Carcinoma | + | Vacuoles, Vesicles |
| Hela | Cervical Carcinoma | - | Floating cells |
| Raji | Burkitt's Lymphoma | + | Secretion, cell clumping |
| P3HR1 | Burkitt's Lymphoma with EBV | + | Secretion, cell clumping |
| H9 | T-Lymphoblastoid | + | Secretion, cell clumping |
| MT-2 | T-Lymphoblastoid | + | Secretion, cell clumping |
| HL-60 | Promyelocytic leukemia | - | |

Mouse cell lines:

| | | | |
|---|---|---|---|
| P388 | Leukemia | + | |
| $P388_{MDR}^+$ | Leukemia | - | |
| ML3 | Differentiated liver | - | |
| TIB 73 | Immortalized liver | + | Vacuoles, Vesicles |
| TIB 74 | SV40-transformed liver | - | Vacuoles, vesicles |
| TIB 75 | Carcinogen-transformed liver | + | Vacuoles, Vesicles |
| Colon-38 | Metastatic colonic carcinoma | - | |
| 197hep | Trangenic mouse liver | + | |

Other cell lines:

| | | | |
|---|---|---|---|
| Vero | Monkey kidney | - | |

Figure 3.

| ODN  | Sequence (5'-3')       | Length | Activity |
|------|------------------------|--------|----------|
| 065H | G A C A C A C G G G T G A T | 14 | + |
| 075H | G A C A C A C G G T T G A T | 14 | − |
| 083H |     C A C A C G G G T G A T | 12 | + |
| 088H |     C A C A C G G G T G A | 11 | + |
| 089H |     C A C A C G G G T G | 10 | + |
| 090H |     C A C A C G G G T | 9 | − |
| 093H |       A C A C G G G T G A T | 11 | − |
| 094H |         C A C G G G T G A T | 10 | − |
| 095H |           A C G G G T G A T | 9 | − |

Figure 4

| ODN | \multicolumn{10}{c|}{POSITION} | Results of CMC Assay |
| --- | - | - | - | - | - | - | - | - | - | - | --- |
| | 1 | 2 | 3 | 4 | 5 | 6 | 7 | 8 | 9 | 10 | 3 uM |
| 089H | C | A | C | A | C | G | G | G | T | G | + |
| 098H | – | – | – | – | – | – | – | – | – | A | – |
| 099H | – | – | – | – | – | – | – | – | – | C | – |
| 100H | – | – | – | – | – | – | – | – | – | T | – |
| 104H | A | – | – | – | – | – | – | – | – | – | – |
| 105H | G | – | – | – | – | – | – | – | – | – | – |
| 106H | T | – | – | – | – | – | – | – | – | – | – |
| 107H | – | – | – | – | – | – | – | – | A | – | – |
| 108H | – | – | – | – | – | – | – | – | C | – | – |
| 109H | – | – | – | – | – | – | – | – | G | – | – |
| 110H | – | – | – | – | – | A | – | – | – | – | – |
| 111H | – | – | – | – | – | C | – | – | – | – | + |
| 112H | – | – | – | – | – | T | – | – | – | – | – |
| 114H | – | C | – | – | – | – | – | – | – | – | – |
| 115H | – | G | – | – | – | – | – | – | – | – | – |
| 116H | – | T | – | – | – | – | – | – | – | – | – |
| 117H | – | – | A | – | – | – | – | – | – | – | – |
| 118H | – | – | G | – | – | – | – | – | – | – | – |
| 119H | – | – | T | – | – | – | – | – | – | – | – |
| 120H | – | – | – | C | – | – | – | – | – | – | + |
| 121H | – | – | – | G | – | – | – | – | – | – | – |
| 122H | – | – | – | T | – | – | – | – | – | – | – |
| 123H | – | – | – | – | A | – | – | – | – | – | – |
| 124H | – | – | – | – | G | – | – | – | – | – | – |
| 125H | – | – | – | – | T | – | – | – | – | – | – |
| 126H | – | – | – | – | – | – | A | – | – | – | + |
| 127H | – | – | – | – | – | – | C | – | – | – | + |
| 128H | – | – | – | – | – | – | T | – | – | – | + |
| 129H | – | – | – | – | – | – | – | A | – | – | – |
| 130H | – | – | – | – | – | – | – | C | – | – | – |
| 131H | – | – | – | – | – | – | – | T | – | – | – |

| ODN | Sequence | IC$_{50}$ (µM) | Self-Complementarity |
|---|---|---|---|
| 065H | G A C A C A C G G G T G A T | ~1 | 8/14 |
| 089H | C A C A C G G G T G | 1.30 ± 0.78 | 8/10 |
| 111H | C A C A C C G G T G | 0.71 ± 0.43 | 8/10 |
| 120H | C A C C C G G G T G | 0.47 ± 0.11 | 10/10 |
| 126H | C A C A C G A G T G | 0.65 ± 0.22 | 8/10 |
| 127H | C A C A C G C G T G | 0.64 ± 0.24 | 8/10 |
| 128H | C A C A C G T G T G | 0.37 ± 0.13 | 10/10 |

Figure 6A

| ODN | Sequence | GC Matches | Activity |
| --- | --- | --- | --- |
| 120H | CACCCGGGTG | 8/10 | + |
| 128H | CACACGTGTG | 6/10 | + |
| 148H | GTGGGCCCAC | 8/10 | + |
| 168H | ATATATATAT | 0/10 | - |
| 001H | ACCACGTGGT | 6/10 | + |
| 167H | CGCGAATTCGCG | 8/12 | + |
| 002H | AGACCACGTGGTCT | 8/14 | + |

Figure 6B

| ODN | Sequence | GC Matches | $T_m$ (°C) | Activity |
| --- | --- | --- | --- | --- |
| 089H | CACACGGGTG | 6/10 | --- | + |
| 589H | CACCCGTGTG | 6/10 | --- | - |
| 089H + 589H | duplex | 7/10 | 52.8 | + |
| 177H | TTTATTATTT | --- | --- | - |
| 677H | AAATAATAAA | --- | --- | - |
| 177H + 677H | duplex | 0/10 | 23.0 | - |
| 196H | | | | |
| 696H | | | | |
| 196H + 696H | duplex | 2/10 | 33.5 | +/- |
| 178H | GCTATTATCG | --- | --- | - |
| 678H | CGATAATAGC | --- | --- | - |
| 178H + 678H | duplex | 4/10 | 43.3 | + |

Figure 8A

Sequence Series 1 (Type 1 Duplexes)

| ODN | Sequence | Length |
|---|---|---|
| 179H | CACGTG | 6 |
| 184H | ACACGTGT | 8 |
| 128H | CACACGTGTG | 10 |
| 185H | CCACACGTGTGG | 12 |
| 180H | TCCACACGTGTGGA | 14 |
| 181H | ACTCCACACGTGTGGAGT | 18 |

Sequence Series 2 (Type 2 Duplexes)

| ODN | Sequence | Length |
|---|---|---|
| 011H | GCATAT | 6 |
| 511H | ATATGC | 6 |
| 012H | AGCATATG | 8 |
| 512H | CATATGCT | 8 |
| 013H | AGCATATGC | 9 |
| 513H | GCATATGCT | 9 |
| 010H | TAGCATATGC | 10 |
| 510H | GCATATGCTA | 10 |
| 014H | TAGCATATGCT | 11 |
| 514H | AGCATATGCTA | 11 |
| 015H | ATAGCATATGCT | 12 |
| 515H | AGCATATGCTAT | 12 |
| 009H | GATAGCATATGCTA | 14 |
| 509H | TAGCATATGCTATC | 14 |
| 008H | AGGATAGCATATGCTACC | 18 |
| 508H | GGTAGCATATGCTATCCT | 18 |

Sequence Series 3 (Type 1 Duplexes)

| ODN | Sequence | Length |
|---|---|---|
| 001H | ACCACGTGGT | 10 |
| 002H | AGACCACGTGGTCT | 14 |
| 003H | GCAGACCACGTGGTCTGC | 18 |

Figure 8B
Type 1 and Type 2
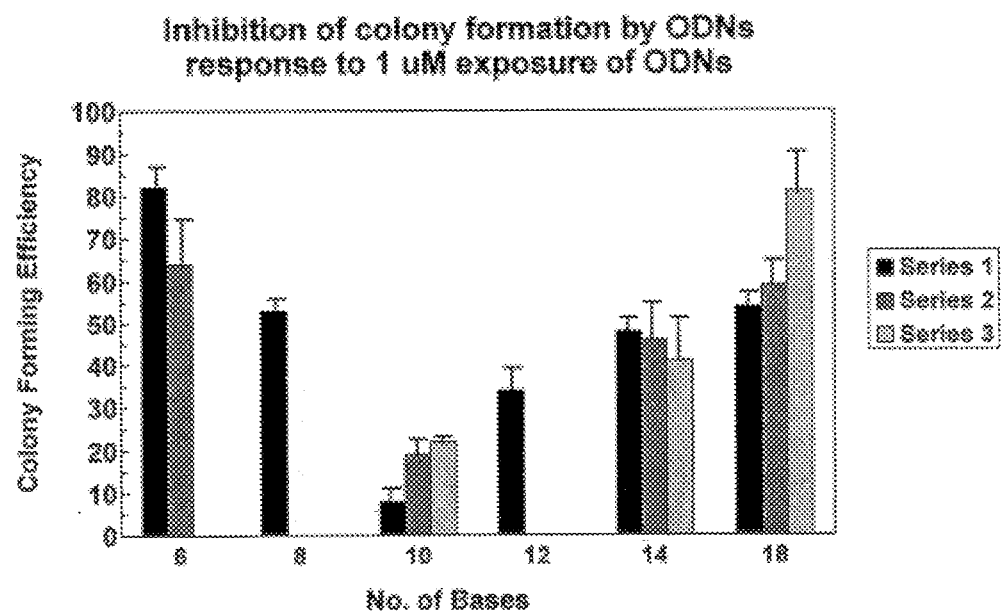
Type 2
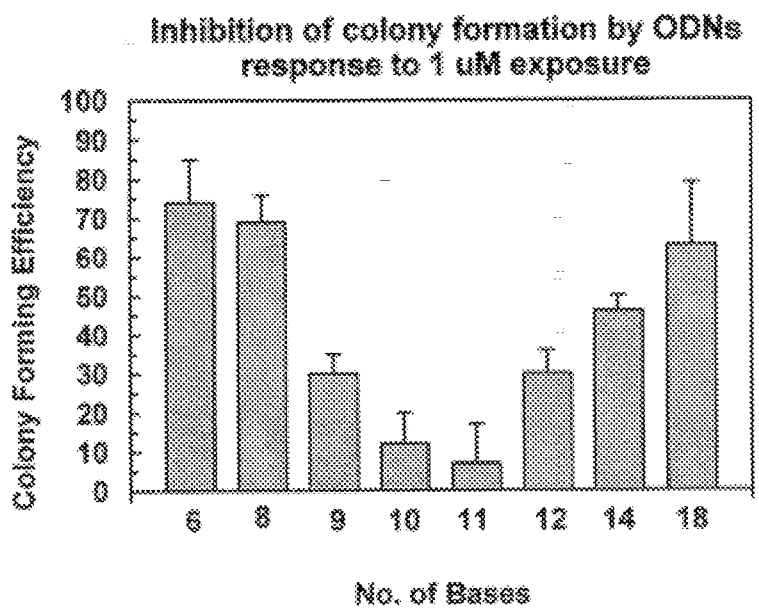

| ODN | Description | Activity | $T_m$(°C) |
|---|---|---|---|
| 065H | No backbone modifications | + | |
| 065.09 | All 2'-OMe nucleotides | - | |
| 065.12 | 1 P-S linkage at position 1.5 | +/- | |
| 065.03 | All P-S linkages | - | |
| 128H | No backbone modifications | + | 46.8 |
| 128.01 | P-S linkage at position 1.5 | +/- | 46.8 |
| 128.02 | P-S linkages at positions 1.5, 2.5, 3.5 | +/- | 41.5 |
| 128.03 | P-S linkages at postions 1.5, 2.5, 3.5, 4.5, 5.5 | - | 35.5 |
| 128.04 | P-S linkage at position 5.5 | +/- | |
| 128.05 | P-S linkages at positions 3.5, 4.5, 5.5, | - | |
| 128.25 | All P-S linkages | - | |
| 180.01 | Self complementary 14-mer, all P-S linkages | - | |
| 128.31 | All RNA backbone | - | |

Figure 10

ODN 128 Sequence: CACACGTGTG

| 3'-Modification | Activity | $IC_{50}$ (μM) |
|---|---|---|
| cholesterol (H) | + | 0.3 |
| hexylamine (F) | - | |
| acridine (S) | - | |
| hexanol (J) | - | |
| hexadecane (312) | - | |
| cholestanol | + | 0.3 |
| ergosterol | +/- | |
| stigmastanol | + | 0.3 |
| stigmasterol | + | 0.3 |
| methyl-lithacholic acid | - | |

Figure 11
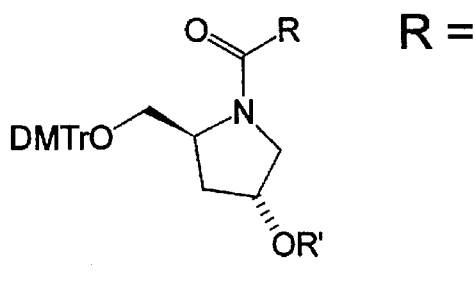
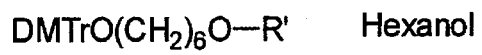 Hexanol
 Hexadecane
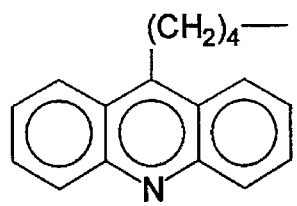 Acridine
sterol supports:
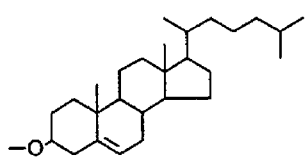 Cholesterol
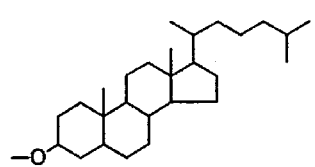 Cholestanol
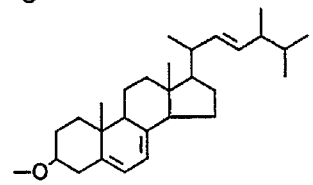 Ergosterol
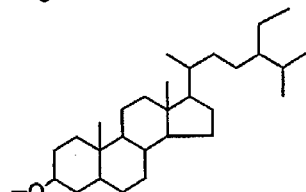 Stigmastanol
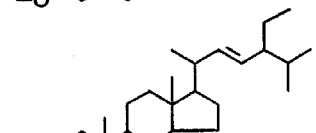 Stigmasterol
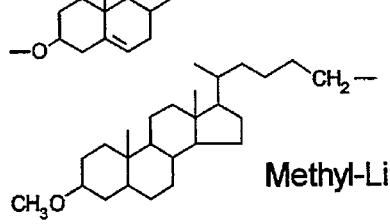 Methyl-Lithocholic acid
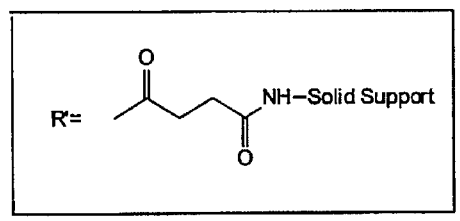

Figure 12

| Structure | Label | Activity | IC$_{50}$ (uM) |
|---|---|---|---|
| RO-CH$_2$-CH(OH)-CH$_2$-NH-R$_1$ | C3 | + | 0.3 |
| RO-CH$_2$-CH(OH)-CH$_2$-CH$_2$-NH-R$_1$ | C4 | + | 0.3 |
| RO-CH$_2$-CH$_2$-N(R$_1$)-CH$_2$-CH$_2$-OH | C2 | + | 0.3 |
| RO-CH$_2$-CH(CH$_2$OH)-CH$_2$-CH$_2$-CH$_2$-CH$_2$-NH-R$_1$ | C6 | +/− | 0.9 |
| RO-CH$_2$-CH(OH)-CH$_2$-NH-CO-CH$_2$-CH$_2$-CO-NH-CH$_2$-CH$_2$-S-S-CH$_2$-CH$_2$-NH-R$_1$ | C15 | − | >1 |
| pyrrolidine (RO, OH, N-R$_1$) | H | + | 0.5 |
| pyrrolidine cis (RO, OH, N-R$_1$) | cis | + | 0.3 |

R = ODN128—O—P(=O)(OH)—

R$_1$ = cholesteryl acetate

Figure 13
| 5'-Modification | | Activity | Ic50 (uM) |
|---|---|---|---|
| ODN128-PO3⁻~~~~~~NH2 | hexylamine | + | 0.3 |
| ~~~~~~OH | hexanol | +/- | 0.5 |
| 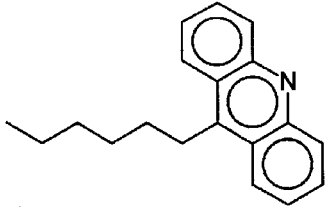 acridine | acridine | - | >3 |
| 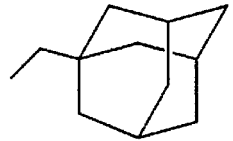 adamantane | adamantane | - | >3 |
| ODN-PO3⁻ | phosphate | + | 0.3 |
| ODN-PO2S⁻ | thiophosphate | +/- | 0.5 |

Figure 14
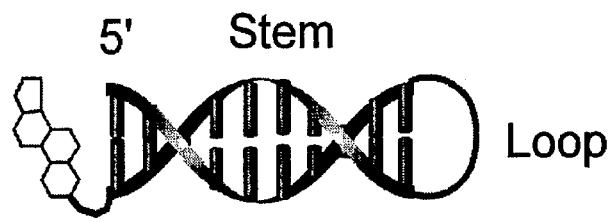
| ODN | | Loop | Activity |
|---|---|---|---|
| 149H | CACCCGGGTG-(OCH$_2$CH$_2$)$_3$-O-CACCCGGGTG | -(OCH$_2$CH$_2$)$_3$-O- | + |
| 204H | CACACGTGTG-(OCH$_2$CH$_2$)$_3$-O-CACACGTGTG | -(OCH$_2$CH$_2$)$_3$-O- | + |
| 205H | CACACGTGTG-GAAA-CACACGTGTG | -GAAA- | + |
| 206H | CACACGTGTG-TTTT-CACACGTGTG | -TTTT- | + |
| 210H | CACACGTGTG-TT-Q*-TT-CACACGTGTG | -TT-Q*-TT- | + |
| 211H | ACACGTGT-TTTT-ACACGTGT | -TTTT- | − |
| 212H | CACGTG-TTTT-CACGTG | -TTTT- | − |
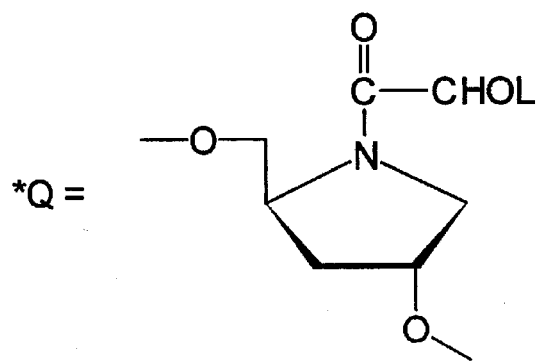
*Q =

STEROL MODIFIED OLIGONUCLEOTIDE DUPLEXES HAVING ANTICANCER ACTIVITY

BACKGROUND OF THE INVENTION

1. Technical Field

The present invention is directed to oligonucleotide duplex compounds which have anticancer activity. The present invention is also directed toward certain modified oligonucleotide compounds which are capable of self-forming a duplex structure, and which have anticancer activity.

2. Brief Description of Background Art

Oligonucleotides have been intensely studied in the prior art as potential chemotherapeutic agents. Methods have been developed for synthesizing oligonucleotides which include the major naturally occurring nucleosides, as well as nucleosides containing modified heterocyclic bases. Methods have also been developed for the synthesis of oligonucleotides which contain modified sugars, as well as modifications in the "phosphate backbone" of the nucleotidic chain. Oligonucleotides containing 2'-O-methyl ribose, arabinose and particularly α-arabinose (U.S. Pat. No. 5,177,196) as well as phosphorothioate linkages serve as examples. Oligonucleotides having various "tails" covalently attached to either their 3'- or to their 5'-ends, or to both, have also been known in the art. Generally speaking, intercalating groups, various kinds of reporter groups and lipophilic groups have been attached to the 3' or 5' ends of the oligonucleotides. Attachment of linking groups to the 3'-end of oligonucleotides, which in turn are attached to an intercalating group, reporter group or lipophilic group, have been described in the prior art. The group derived from the linking group amino-2,3-propane diol serves as an example. A method of synthesizing oligonucleotides on a solid phase support, using optically pure 2-(hydroxymethyl)-4-hydroxy-pyrrolidine as a group which links the growing oligonucleotide chain to the solid support as well as to a desired "tail moiety", such as a lipophilic moiety, is described in a patent application having one or more inventors in common with the present application. Descriptions of syntheses of 3'-cholesterol or 3'-acridine modified oligonucleotides can be found in the articles: Gamper, H. B., Reed, M. W., Cox, T., Virosco, J. S., Adams, A. D., Gall, A., Scholler, J. K., and Meyer, R. B. (1993) Facile Preparation and Exonuclease Stability of 3'-Modified Oligodeoxynucleotides. *Nucleic Acids Res.* 21 145–150; and Reed, M. W., Adams, A. D., Nelson, J. S., and Meyer, R. B.,Jr. (1991) Acridine and Cholesterol-Derivatized Solid Supports for Improved Synthesis of 3'-Modified Oligonucleotides. *Bioconjugate Chem.* 2 217–225 (1993).

As far as potential chemotherapeutic agents, the so-called "antisense" oligonucleotides have been the focus of the most intense research, since such compounds, if designed to be complementary to a target RNA sequence, promise the ability to hybridize with messenger RNA, and therefore interfere with the synthesis of distinct proteins within the cell. To this date however, results with antisense oligonucleotides (ODNs) have been somewhat disappointing in terms of successful chemotherapy. Nevertheless some oligonucleotides have been demonstrated to act as anti-cancer agents by an anti-sense mechanism, and one particular anti-sense oligonucleotide is understood to be in clinical trial in the United States.

The art pertaining to the synthesis of chemotherapeutic agents against cancer is even older than the art pertaining to the chemistry and molecular biology of nucleic acids and their components. Whereas numerous cancer chemotherapeutic agents have been developed in the art, have been described in the scientific literature and have been patented, and whereas several are currently used for treatment of cancer in humans, much remains to be desired in this field in terms of efficacy, and selective cytotoxicity to cancer cells. There are also many types of cancers which are more-or-less unaffected by currently available chemotherapeutic agents. There are also cancer cells which although originally vulnerable to certain chemotherapeutic agents, develop resistance to them. There are known cancer cell lines having resistance to multiple drugs (multiple drug resistance, MDR). As far as the present inventors are aware, the present invention provides, for the first time, modified oligonucleotidic compounds which show anticancer activity in other than an "anti-sense" manner, and which show selective toxicity toward certain cancer cell lines, and to certain cancer cell lines with multiple drug resistance.

SUMMARY OF THE INVENTION

It has been discovered in accordance with the present invention that certain modified oligonucleotide stable duplex compounds have anti-cancer activity, and specifically that such compounds show selective toxicity toward certain specific cancer cells, including some cancer cells which have multiple drug resistance (MDR) against certain established cancer chemotherapeutic agents.

The oligonucleotide duplex compounds of the invention have the following essential structural features:

(a) each strand of the duplex consists of approximately 8 to 18 nucleotide units, and each strand is sufficiently complementary to the other strand so as to form a substantially stable duplex at physiological temperature by Watson Crick type base pairing;

(b) the 3'-end of the oligonucleotide is linked, with or without a linker moiety which may be of up to approximately 12 atom length, to a lipophilic moiety, preferably of the general structure of Formula 1.

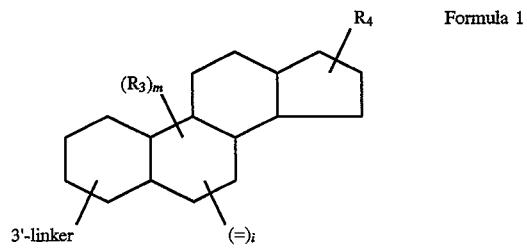

Formula 1 where the 3'-end of the ODN is linked, with or without the linker moiety, to the A ring of asteroid skeleton, $R_3$ is H, $C_1$–$C_6$ alkyl, or $C_2$–$C_6$ alkenyl and is attached to the A, B or C ring of the steroid skeleton, m is an integer having the values 0 to 4, i is an integer having the values 0 to 4, and $R_4$ is H or a $C_1$ to $C_{15}$ alkyl group, or a $C_2$ to $C_{15}$ alkenyl group having 1 to 3 double bonds and the $R_4$ group is attached to the D ring of the steroid skeleton.

The term "lipophilic group" in this regard is well understood by those skilled in the art of medicinal chemistry, and means a group whose chemical make-up provides it with high affinity to lipid phase matter. The term "lipophilic group", in the context of being attached to an oligonucleotide, refers to a group having high hydrocarbon content thereby giving the group high affinity to lipid phases.

The 3 major types of modified oligonucleotides which are capable of forming the above-described duplexes and which are within the scope of the invention, are illustrated in FIG. 1. Type 1 ODN is composed of two identical self-complementary, or substantially self-complementary strands, with each strand having the lipophilic tail, so that upon duplex formation both ends of the duplex have the lipophilic tail.

Type 2 ODN is composed of two different but complementary, or substantially complementary strands, preferably with the 3'-end of each strand having a lipophilic tail.

Type 3 ODN is a single self complementary strand, which forms a duplex with itself, including a "hairpin" turn. A variation of the Type 3 ODN within the scope of the invention is a single self-complementary modified ODN wherein the "hairpin turn" region is something other than a conventional oligonucleotide moiety. For example, the hairpin turn region may be an alkylene group (—CH$_2$)$_p$—), or the hairpin turn region may consist of a polyethyleneglycol moiety' e. g of the formula —(O—CH$_2$CH$_2$)$_p$— (where p is an integer between 3 to 10). As still further variation the hairpin turn region may include an amine functionality, e. q. of the formula [O—CH$_2$CH$_2$)$_q$—NH—CH$_2$CH$_2$—(O—CH$_2$CH$_2$)$_r$, to which another lipophilic group may be optionally attached, through the amine functionality, and where q and r are integers the sum of which is 2 to 10. Also the hairpin turn region may include more than one amine functionality. In general terms the hairpin turn region contains approximately 3 to 8 nucleotides, or if it is a region consisting of other than nucleotides, it is a covalently linked chain of approximately 6 to 30 atoms which allows the 7 to 18 nucleotide long complementary regions of the oligonucleotide to hybridize with Watson-Crick type base pairing.

FIG. 1 also illustrates a generalized structure (Formula 2), showing a single strand of the duplex modified oligonucleotides of the present invention (before duplex formation occurs) wherein B is a major naturally occurring nucleotide base residue selected from the group consisting of 1-N-uracil, 1-N-thymine, 1-N-cytosine, 9-N-adenine and 9-N-guanine residues;

the wavy line between the sugar and the base B represents a glycosidic bond of either α or of β configuration;

X is S or O, with the understanding that X=S represents a phosphorothioate linkage and that there are no more than 3 phosphorothioate linkages in each strand of the duplex;

R$_1$ is H, OH, or F;

R$_2$ is H, or F;

W is H or YO(OH)XP-;

Y is H, alkyl of 1–20 carbons, branched chain alkyl or cycloalkyl of 3 to 25 carbons, (CH$_2$)$_s$OH, (CH$_2$)$_s$NH$_2$, hydroxy branched chain alkyl or hydroxy cycloalkyl of 3–25 carbons, amino branched chain alkyl of 3 to 25 carbons or amino cycloalkyl of 3 to 25 carbons, or a lipophilic group which may be connected to the phosphate residue with an appendant connecting group of 1 to 10 atom length, s is an integer between 2–25;

n is an integer having a value between 8 and 18; the remaining symbols have the definitions provided in connection with Formula 1, and the heterocyclic bases B are such that the strand forms a substantially stable duplex at physiological temperature by Watson Crick type base pairing, either with itself (self-complementary) or with another strand which also has the structure defined by generalized Formula 2. Pharmaceutically acceptable salts of the oligonucleotides defined above are also within the scope of the invention. Generally speaking, whenever the present description defines an alkyl group, cycloalkyl or branched chain alkyl is also included in the definition, unless the description specifically states otherwise.

The features of the present invention can be best understood together with further objects and advantages by reference to the following description, taken in connection with the accompanying drawings which include chemical formulas, tables and graphs.

BRIEF DESCRIPTION OF THE DRAWINGS

FIG. 1 includes general Formula 2 and schematically depicts three types of modified oligonucleotide (ODN) duplexes in accordance with the present invention.

FIG. 2 is a table showing the cytotoxic activity in several cancer cell lines of a specific embodiment, designated "065H", of the ODNs of the present invention.

FIG. 3 is a table showing the cytotoxic activity, or lack thereof, in a cell morphology change (CMC) assay, of certain modified ODNs within the scope and outside of the scope of the present invention.

FIG. 4 is a table showing the cytotoxic activity, or lack thereof, against Hepatoma G2 (HepG2) cell lines in the cell morphology change (CMC) assay, of certain modified 10 mer ODNs within the scope and outside of the scope of the present invention.

FIG. 6A is a table disclosing structures of specific self-complementary ODNs within the scope and outside of the scope of the present invention, showing the results of the cell morphology change (CMC) assay in HepG2 cells.

FIG. 6B is a table disclosing structures of specific ODN pairs within the scope and outside of the scope of the present invention, showing the results of the cell morphology change assay in HepG2 cells.

FIG. 8A is a table disclosing the structures of certain ODNs within the scope and outside of the scope of the present invention.

FIG. 8B contains two graphs showing the results of a clonogenic assay with HepG2 cells as a function of the length of the ODNs.

FIG. 10 is a table disclosing the structures of certain ODNs within the scope and outside of the scope of the present invention, and showing the results of a cell morphology change assay in HepG2 cells, as a function of variations in the structure of the 3'-tail of the ODNs.

FIG. 11 shows in a tabulated format the structures of several solid support intermediates employed in the synthesis of ODNs within the scope and outside of the scope of the present invention.

FIG. 12 shows in a tabulated format the structures of several linking moieties incorporated between a cholesterol moiety and the 3'- end of ODNs, some of which are within the scope and some of which are outside of the scope of the present invention; the figure also shows the results of a cell morphology change assay in HepG2 cells on these ODNs.

FIG. 13 is a table disclosing the structures of certain ODNs within the scope and outside of the scope of the present invention, and showing the results of a cell morphology change (CMC) assay with HepG2 cells, as a function of variations in the structure of the 5'-tail of the ODNs.

FIG. 14 is a table disclosing the structures and activity of Type 3 ODNS.

DETAILED DESCRIPTION OF THE INVENTION

Figure 5:
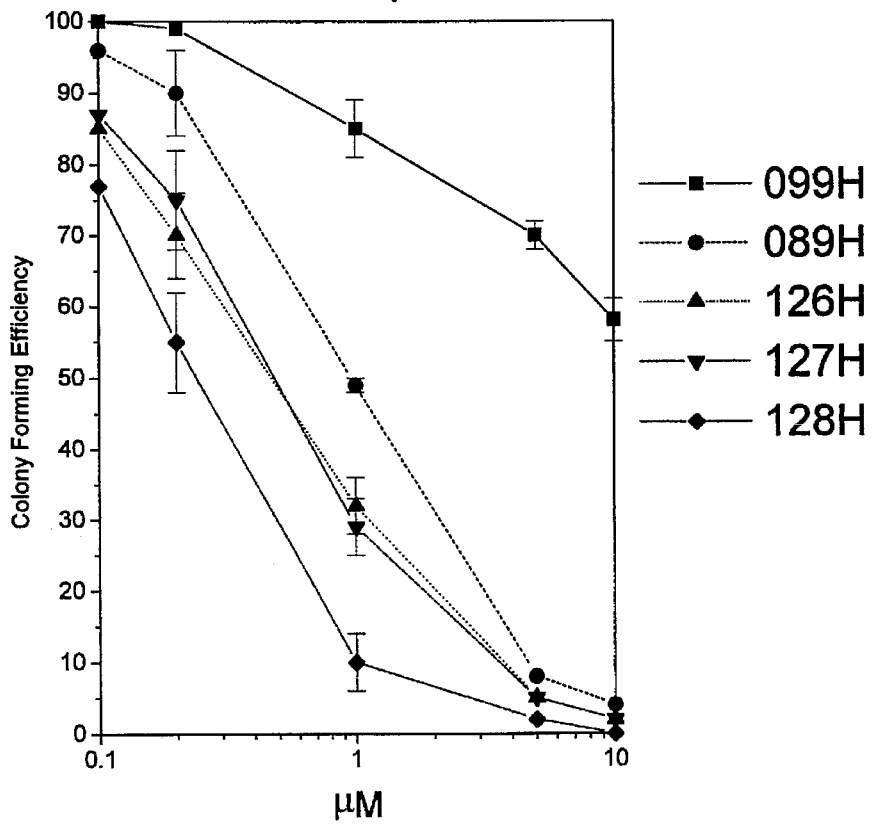
FIG. 5 is a table and graph showing the ability of exemplary ODNs within the scope of the present invention to inhibit colony formation of HepG2 cells in a clonogenic assay.

It has been discovered in accordance with the present invention that stable duplex oligonucleotides (ODNs) which have the structures described above in the Summary of the Invention and shown on FIG. 1, have significant selective cytotoxic activity against certain cancer cell lines, including some cancer cell lines which have resistance to several established anticancer agents (cells with multiple drug resistance, MDR). The cytotoxic activity of the duplex ODNs was demonstrated by a qualitative cell morphology change (CMC) assay, in several cell lines, including the immortalized HepG2 cell line, and also by a quantitative clonogenic (colony formation) assay conducted with the HepG2 cell line. Although the experimental procedures for conducting these assays is well known in the art, the specific procedures employed in the assays involving the compounds of the invention are described in detail below.

FIG. 2 illustrates the cytotoxic activity of an exemplary ODN duplex of the present invention which bears the arbitrary designation number 065H. Because of the large number of exemplary ODNs of the present invention, a "shorthand" designation system is utilized throughout the instant specification, which is explained as follows. Each oligonucleotide sequence prepared in connection with the present invention has been assigned a three digit number. The number, such as "065" being arbitrary, does not reveal the sequence of the ODN, which is disclosed elsewhere, either in the written specification or in the drawing figures or "tables", in the manner customary in the art. Unless their structure is specifically noted otherwise, all disclosed specific examples of oligonucleotides are 2'-deoxyribosides containing the major naturally occurring bases. The sequence of the ODNs is written (as customary in the art) from left to right beginning with the 5'-OH end of the ODN. Unless there is specific description or explanation describing a different structure, the three digit arbitrary number (such as "065"), and the corresponding sequence indicate that the 5'-OH end of the ODN is unmodified, and that the ODN contains no phosphorothioate linkage. In accordance with the present invention the 3'-end of the ODN is always modified with a tail. The currently preferred tail comprises a cholesterol moiety which is linked to the 3'-phosphate end of the ODN through a carbonyl group, attached to the ring nitrogen of a moiety derived from 4-hydroxy-2-hydroxymethylpyrrolidine. The structure of this preferred tail, including the preferred linker group is shown by Formula 3. This "tail", including the linker group shown by Formula 3 is symbolized by the letter H next to the arbitrary 3 digit designation number. The majority of specific examples of compounds of the invention can be described by the 3 digit designation number followed by an "H", because they are ODNs modified only at the 3'-end by the modification "H". A period and number following the first 3 digit designation number of an ODN means an additional modification of the molecule and is accompanied by appropriate explanation. When such modification does not affect the 3'-end, then unless stated or shown otherwise, the particular ODN still has the "cholesterol tail" shown by Formula 3. An ODN which is complementary to another ODN in accordance with the invention is designated by a number which differs by 500 from the number of its complementary partner. Thus, ODN 089H and 589H are complementary (their structures are shown in the table of FIG. 6B) and both have the "cholesterol tail" shown by Formula 3.

Formula 3

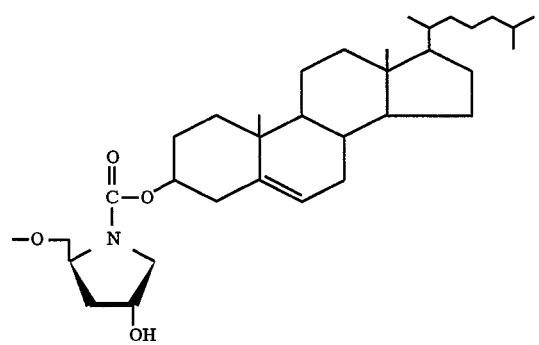

The sequence of the ODN 065H is disclosed in the table of FIG. 3, and the activity of this compound in the cell morphology change (CMC) assay against several immortalized tumor cell lines is disclosed in FIG. 2. The CMC assay is a qualitative assay in which a "+" sign indicates that the tested ODN is strongly cytotoxic in the tested concentration, a "+/−" sign shows weak activity, and a "−" sign shows that the compound is inactive in the assay in the tested concentration. The particularly significant results shown in FIG. 2 are that this ODN of the invention is cytotoxic against specific but not all tumor cell lines, and that some of the cell lines against which the ODN is active, such as colon carcinoma cell lines, hepatoma cell lines, as well as the naso-pharyngeal KB cell line with multiple drug resistance ($KB_{MDR}+$) that are generally known to be relatively immune to conventional cancer chemotherapeutic agents. Moreover, it is particularly noteworthy that the ODN is active against the naso-pharyngeal KB cell line with multiple drug resistance ($KB_{MDR}+$) but not against the same cell line which has not acquired multiple drug resistance.

FIG. 3 shows the structure of several ODNs which were prepared and tested in connection with the present invention. The suffix "H" indicates that each of these ODNs have the "cholesterol tail" of Formula 3 at the 3' phosphate end. However, only those ODNs which are capable of forming a substantially stable duplex by Watson Crick type base pairing are within the scope of the invention, and are active. In this regard it should be kept in mind, that as is well known, a G-C pair provides more "strength" or stability to a duplex than an A-T pair, and further that G-A and A-G mismatches allow more stable duplex formation than C-T and T-C mismatches. Thus a certain number of mismatches, depending on their nature can be present in the compounds of the invention, as long as the respective duplex is substantially stable. It can be seen from the table of FIG. 3 that the 10 mer 089H is sufficiently self-complementary (with only two GA mismatches) and this ODN is active in the CMC assay. The duplex formed from the 14 mer ODNs 065H is substantially stable, because it incorporates the substantially self-complementary 10 mer "core" sequence of the 089H ODN. Thus the further two mismatches of G-T and A—A at the ends of this ODN are not sufficient to destabilize the duplex of ODN 065H. However, one more mismatch, as in ODN 075H, destabilizes the duplex, and ODN 075H is inactive, and outside of the scope of the invention.

The table of FIG. 4 shows a number of 10 mer ODNs, each with the 3'- end cholesterol tail of Formula 3, which were prepared and tested in the CMC assay against HepG2 cells at 3 μmolar concentrations, in connection with the present invention. The ODNs shown in FIG. 4 represent systematic variations of the sequence of ODN 089H. A dash ("–") in this table means that the nucleotide in the respective position is unchanged relative to ODN 089H. Six of the ODNs shown in the table of FIG. 4 are active against the HepG2 cell line. Further results of a quantitative clonogenic assay in HepG2 cell lines testing the six 10 mer ODNs shown active in FIG. 4, plus the 14 mer 065H, are disclosed in the table and graph of FIG. 5. A lower $IC_{50}$ concentration indicates a greater degree of inhibition of colony formation, therefore greater cytotoxic activity. FIG. 5 also correlates the $IC_{50}$ as a quantitative measure of cytotoxic activity with the degree of self-complementary nature of the 10 mer ODN. It is clear that the two most active ODNs within this series are 120H and 128H, which are completely self-complementary with 10 matching base pairs.

Those ODNs disclosed in FIGS. 3, 4, and 5 which are capable of forming substantially stable duplexes with themselves, correspond to the Type 1 ODNs of the present invention, as disclosed in FIG. 1. These ODNs form their stable complexes at physiological temperatures merely by being in an aqueous solution, and therefore the single stranded ODNs as well as the respective duplexes are within the scope of the present invention.

FIG. 6 A discloses seven self-complementary ODNs of Type 1 (as shown in FIG. 1) having the 3'-end "cholesterol tail" of Formula 3. The figure correlates the number of G-C pairs of these ODNs with their activity in the HepG2 CMC assay. As FIG. 6A reveals, all of these ODNs, except for 168H, have a substantial number of G-C matches. Therefore, they form substantially stable duplex structures at physiological temperature and are active in the CMC assay. ODN 168H is comprised only of A and T bases, and is therefore bonded only by much weaker bonds to form a duplex, the duplex is not substantially stable as required for the present invention, and this ODN is inactive in the CMC assay.

FIG. 6B discloses sequences of four ODN pairs which are fully complementary to one another, so as to form Type 2 duplex structures, as shown in FIG. 1. Each of these ODNs have the preferred 3'-end "cholesterol tail" of Formula 3. The melting temperature ($T_m$) of these four duplexes is listed together with the number of G-C pairs in each duplex and the results obtained in the HepG2 CMC assay. As is known in the art, the melting temperature of an oligonucleotide or polynucleotide duplex is defined as that temperature at which 50% of the respective oligonucleotide or polynucleotide is dissociated from its duplex, Watson Crick hydrogen bonded form. A higher melting temperature ($T_m$) means a more stable duplex. As is known further, the melting temperature of an oligonucleotide or polynucleotide is dependent on the concentration of the nucleotide in the solution in which the melting temperature is measured, with higher concentrations resulting in higher measured melting temperatures. The melting temperatures indicated in FIG. 6B were measured at 3 μmolar concentration of the respective ODN (see specific example below), which is in the same range of concentration in which the clonogenic effects were measured. It can be seen that among the four duplexes shown in the table of FIG. 6B only the duplex formed from ODNs 177H and 677H is inactive. This duplex has no bonding G-C pair, and a melting temperature which is 23.0° C. The duplex formed from ODNs 196H and 696H has 2 bonding G-C pairs, a melting temperature of 33.5° C., and the duplex is weakly active in the CMC assay.

Again, it is apparent from the foregoing that duplexes which are substantially stable at physiological temperature are within the scope of the present invention, and are active in the assay. Generally speaking, an oligonucleotide duplex which otherwise meets the structural requirements of this invention, can be considered substantially stable at physiological temperature, and therefore within the scope of the invention, if its melting temperature at approximately 3 μmolar concentration in phosphate buffered saline is not lower than approximately 25° C.

It is further noteworthy regarding the structures and results disclosed in FIG. 6B that ODN 089H is substantially self-complementary and can hybridize with itself with 8/10 base pair matches. Of these 8 base pairs, 6 are G-C and 2 are A-T. The duplex is substantially stable because of the relatively high G-C content and because the G-A and A-G mismatches are well tolerated. ODN 089H is active in the CMC assay. ODN 589H is complementary to ODN 089H, and as such should be self-complementary to itself, also with 8/10 base pair matches. The mismatches in this ODN however are C-T and T-C pairs which are poorly tolerated. For this reason ODN 589H does not hybridize to a substantially stable duplex with itself, and is inactive in the CMC assay. A duplex formed from ODN 089H and ODN 589H, however is fully complementary as far as base pair matches are concerned, has 7 G-C pairs, and a melting temperature of 52.8° C. The duplex of this pair of nucleotides is active in the CMC assay.

In light of the foregoing, substantially stable duplexes formed from a pair of oligonucleotides which are complementary, or nearly complementary to one another, and which otherwise meet the structural requirements of this invention, are also within the scope of this invention, as well as the pairs of such oligonucleotides even if they are separated, provided they are capable of forming the aforesaid substantially stable duplexes. ODNs within this aspect of the invention are depicted as Type 2 in Formula 1.

Figure 7:
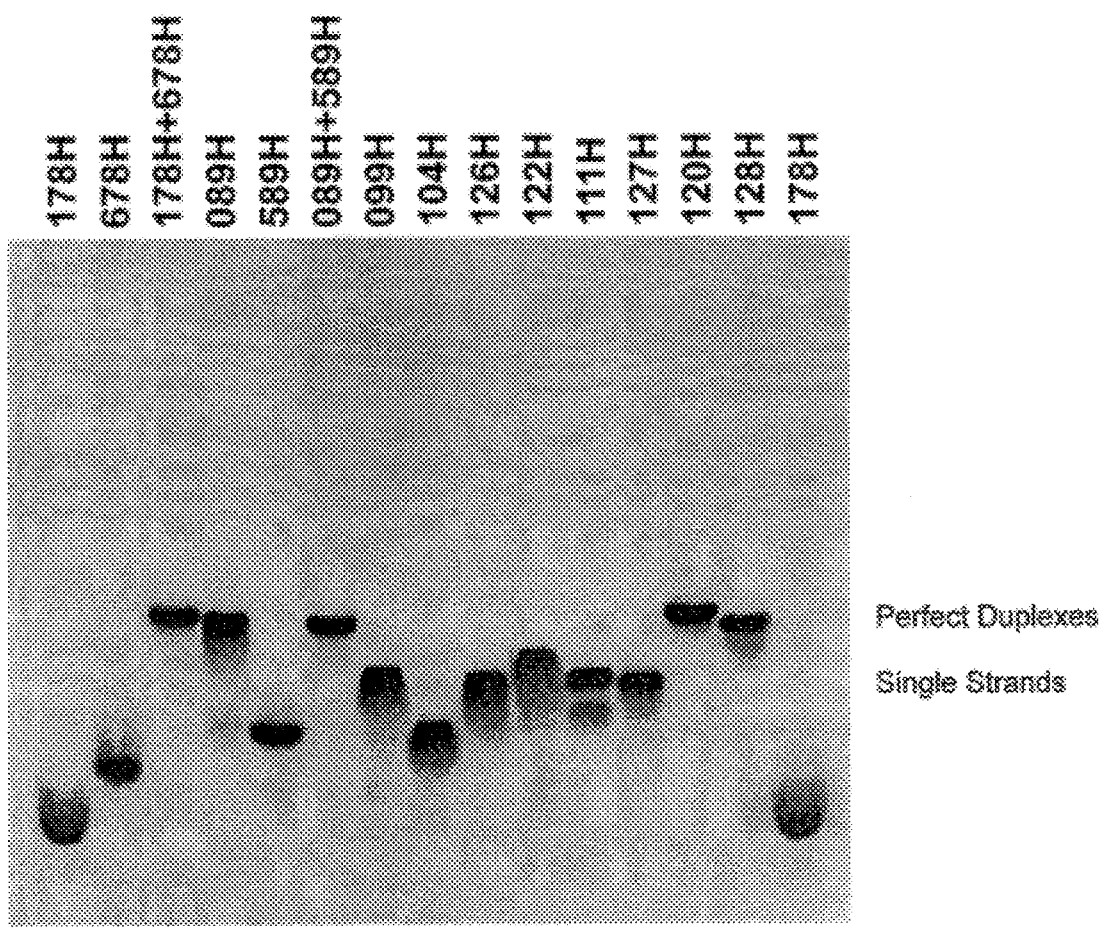
FIG. 7 is a representation of results of a polyacrylamide gel electrophoresis under non-denaturing conditions of specific ODNs within the scope and outside of the scope of the present invention.

FIG. 7 represents the results of an actual polyacrylamide gel electrophoresis test which was conducted under non-denaturing conditions with several ODNs, and as applicable with complementary ODN pairs, prepared in connection with the present invention. Each spot in the electrophoresis represents the migration of the respective ODN, or of complementary ODN pairs, indicated by the respective designation number. The structures of the ODNs shown in this figure are disclosed in the several other tables of this application. As is known in the art, in this electrophoresis test single strands of oligonucleotides migrate faster than perfect duplexes, and oligonucleotides which at the temperature of the test are neither fully dissociated, nor fully associated into a duplex migrate somewhere in between the perfect single strands and perfect duplexes. The results of this test confirm that those ODNs of the invention which are most active also form the most stable duplexes, whereas inactive ODNs, such as 178H and 678H migrate substantially as single strands. A combination of ODNs 178H and 678H, which form a complementary pair with activity in the CMC assay, migrates as a substantially perfect duplex.

The oligonucleotides within the scope of the present invention have approximately 8 to 18 nucleotide units. FIG.

8A discloses the structures of a plurality of ODNs prepared in connection with the present invention, including Type 1, and Type 2 ODNs, each of which has a 3'-end "cholesterol tail", as defined in Formula 3. FIG. 8B includes graphs showing the quantitative results of the clonogenic assay conducted for these ODNs with HepG2 cells. As it was noted in connection with FIG. 5, less colony formation means greater inhibition and greater cytotoxicity of the tested ODNs toward this immortalized cancer cell line. The most active ODNs within the scope of the invention have approximately 10 nucleotide units, with the range of 8 to 14 units being preferred.

With respect to modifications, or lack thereof, of the basic nucleoside base, 2'-deoxyribose and phosphate "backbone" of the ODNs of the present invention, the following is noted. Modifications of the heterocyclic bases, such as replacement of some of the bases with heterocyclic bases other than thymine, cytosine, adenine and guanine are within the scope of the invention provided the resulting oligonucleotides still meet the other structural requirements of the invention, and provided the ODNs still form substantially stable duplexes.

Figures 9A, 9B:
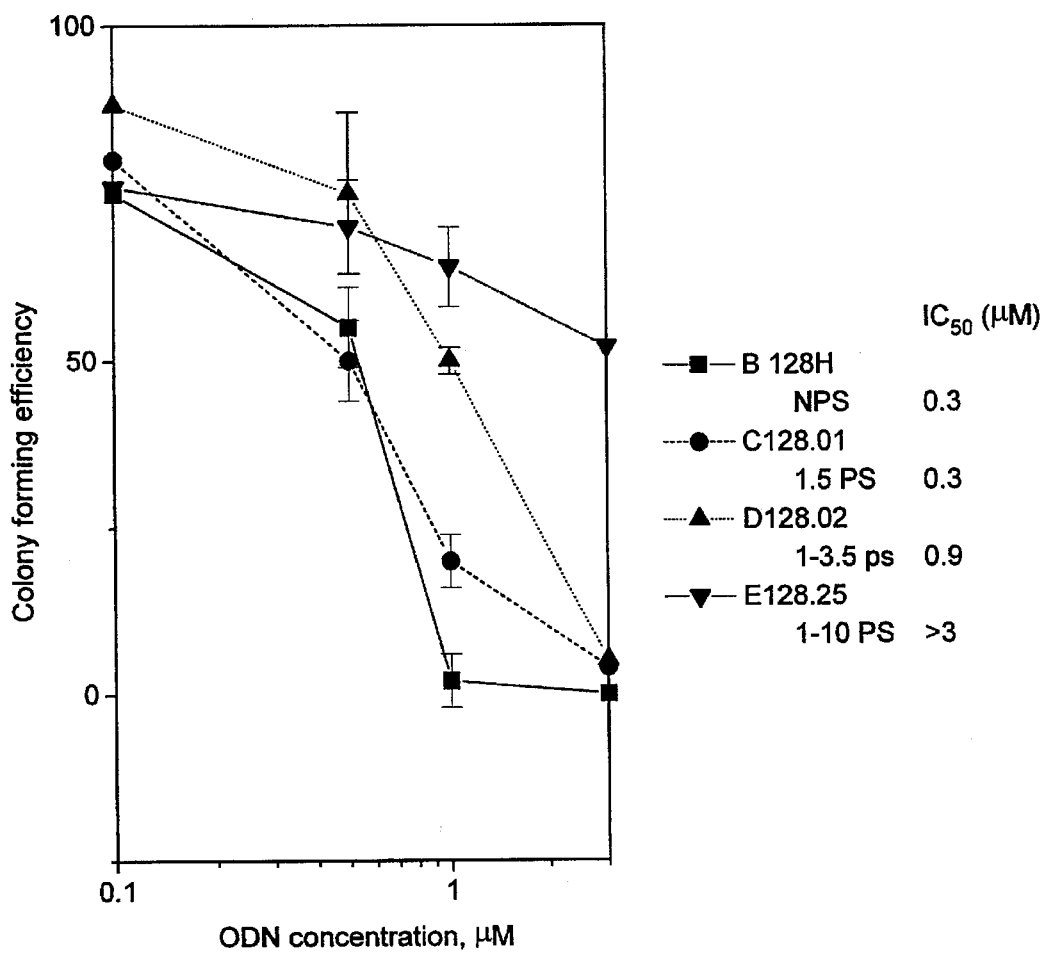
FIG. 9A is a table disclosing the structures of certain ODNs within the scope and outside of the scope of the present invention, and the activity of said ODNs in the HepG2 CMC assay.
FIG. 9B is a graph showing the results of a clonogenic assay with HepG2 cells, as a function of variations in the structure of the "phosphate backbone" of the ODNs.

Regarding modification of the "sugar" backbone, ODNs containing all ribonucleotides (ODN 128.31) are outside of the scope of the present invention. This is indicated on FIG. 9A where several ODNs which have the same basic sequence structure and 3'-end "cholesterol tail" of Formula 3 as ODN 065H, are listed together with their respective activity in the CMC assay of HepG2 cells. ODNs corresponding to ODN 128H in sequence and tail (see FIG. 4) and to ODN 180H in sequence and tail (see FIG. 8A) but modified in other aspects are also disclosed in FIG. 9A. The figure shows that ODNs having all 2'-O-methyl nucleotides are outside of the scope of the present invention (see ODN 065.09), as are ODNs having an all phosphorothioate backbone (see ODN 065.03 and ODN 128.25). However, ODNs having up to approximately 3-phosphorothioate linkages are within the scope of the invention. ODNs including $\alpha$ and $\beta$ arabinosides, preferably $\alpha$ arabinosides, as well as ODNs including 2'-deoxy-2'-fluoro ribose sugars are also included within the scope of the invention.

Presently preferred ODNs of the invention however contain no phosphorothioate linkages. This is shown by the quantitative clonogenic assay shown in the graph of FIG. 9B, where the activity of several ODNs having the sequence of ODN 128H, but also including phosphorothioate modifications, is indicated. As it can be seen in the graph, among the compounds shown in the graph ODN 128H, which includes no phosphorothioate linkage, is the most active.

The ODNs of the present invention must have a unique lipophilic tail at the 3'-end. The lipophilic tail can be attached to the phosphate group at the 3'-end either directly, that is without any connecting or linker group, or through a connecting or linker group. The nature of the linker is not particularly critical; however it is preferred that the linker not have a length of more than 12 atoms. Thus, the lipophilic group may be connected to the 3'-terminus of the oligonucleotide through a linker group which itself may incorporate various linkages such as a phosphorothioester or phosphoramidate linkage, shown here below for the specific example where the lipophilic group is cholesterol. The oxygen atom of the hydroxyl function of cholesterol which is attached to the A ring of the steroid skeleton is marked with an asterisk.)

Oligo - 3'—OP(OH)O—S—$(CH_2)_t$—NHCO—O*chol
(phosphorothioester)

Oligo - 3'—OP(OH)O—NH—$(CH_2)_t$—NHCO—O*chol
(phosphoroamidate)

In the foregoing two examples t ranges between 1 to approximately 8 in value and the respective groups —S—$(CH_2)_t$—NHCO and —NH—$(CH_2)_t$—NHCO— should be considered the linkers. In these examples, these groups are derived from a bifunctional molecule which allows covalent linking of the lipophilic group (such as cholesterol) to the phosphate or phosphorothioate terminus of the oligonucleotide. The bifunctional molecule may, for example, have an amine and a thiol, an amine, and a hydroxyl, or a thiol and a hydroxy functionality, which are then reacted with the lipophilic group and with an activated form of the 3'-phosphate terminus. The linker group can also be defined (and will be understood as such by those skilled in the art) as a group which covalently connects the lipophilic group to the phosphate or phosphorothioate terminus without destroying the ability of the connected lipophilic group to perform its intended function. The linker group can also be a branched chain alkyl, cycloalkyl, or heteroalkyl group.

Alternatively, cholesterol (or other lipophilic group) may be connected to the 3' terminus of the oligonucleotides of the invention through a linking molecule (linker) that has a primary hydroxyl, secondary hydroxyl and an amine functionality, each such function having different reactivity. An example for such a trifunctional linking molecule is 4-hydroxy-2-hydroxymethylpyrrolidine, another example is 3-amino-1,2-propanediol. When such a trifunctional linking molecule is used, the cholesterol or other lipophilic group is usually attached to the primary amine through still another linking moiety, and the primary hydroxyl group of the linking molecule (linker) is usually attached to the 3'-phosphate terminus of the oligonucleotide. The secondary hydroxyl group of the just described linking molecule (such as 4-hydroxy-2-hydroxymethylpyrrolidine or 3-amino-1,2-propanediol) may be utilized to attach the molecule to a solid phase support allowing step-by-step oligonucleotide synthesis on an automatic synthesizer, in accordance with the state-of-the art. In fact, using a synthetic process on a solid phase support, utilizing such a trifunctional linker molecule is the preferred method for synthesizing the oligonucleotides of the present invention.

An example of cholesterol linked to the 3'-terminus of the oligonucleotide via a carbamate linkage and 4-hydroxy-2-hydroxymethylpyrrolidine is shown by Formula 3. The carbamate linkage, linking cholesterol with the amine function of 4-hydroxy-2-hydroxymethylpyrrolidine is derived from chloroformate. In a broad sense the entire trifunctional linking molecule plus the "CO" group of this example serve as the linker moiety, covalently attaching the exemplary cholesterol, or other lipophilic group, to the 3'-phosphate terminus of the oligonucleotide.

Alternatively, a lipophilic group can be connected by a "carbamate" linkage, or by some other group, to the amine function of 3-amino-1,2-propanediol which in turn is linked to the 3'-phosphate terminus with its primary hydroxyl group.

The table of FIG. 12 illustrates various exemplary trifunctional linking moieties (linkers) which attach the 3'-phosphate terminus of an ODN having the sequence of ODN 128 to a cholesterol moiety. This is indicated in the figure, where the symbol R stands for the 3' phosphate terminus of ODN 128 and the symbol $R_1$ stands for the cholesterol moiety bearing a carbonyl group on its hydroxyl function. In each of these linking moieties the free hydroxyl group can be used to attach the linker to a solid phase support, for convenient oligonucleotide synthesis in an automatic ODN synthesizer. The biological activity of the 128 ODNs bearing these linking moieties in the HepG2

CMC assay is also shown in FIG. 12. The results confirm that the nature of the linking molecule is not critical for the anticancer activity of the ODN; only the ODN with a linker which has a 15 atom long chain between the lipophilic (cholesterol) group and the 3' phosphate terminus was inactive in this assay.

Referring now to the table shown in FIG. 11, the structures of solid phase supports attached to various possible lipophilic groups, through various possible linking moieties (linkers) are disclosed. As is known, the solid phase support is a functionalized porous glass support, which is represented in this figure by the symbol R'. The functionalized solid phase support may be attached to a bifunctional molecule, such as dimethoxytrityl protected hexanediol, on which an oligonucleotide can be built after removal of the dimethoxytrityl group. More preferably however, in accordance with the present invention, the functionalized solid phase support is connected to the secondary hydroxyl group of 2-dimethoxytrityl-4-hydroxymethylpyrrolidine. Immediately below here follows a description of the presently preferred chemistry employed in the synthesis of the oligonucleotides of the invention, with particular emphasis on the synthesis of the linking molecule coupled to the lipophilic (tail) moiety coupled to the solid phase support.

The presently preferred linking molecule (2S, 4R)-4-hydroxy-2-hydroxymethyl-pyrrolidine (also identifiable as 4-hydroxy-(2S-trans)-2-pyrrolidinemethanol or trans-4-hydroxy-L-prolinol) is readily prepared from commercially available N-CBZ-L-hydroxyproline (Sigma Chemical Company). Reduction of the N-CBZ-L-hydroxyproline utilizing a procedure similar to that described by Stanfield et al., J. Org. Chem. 46: 4799 (1981) is readily accomplished in a borane-THF complex (Aldrich Chemical Co.). This reduction proceeds with retention of the optical purity of the compound. After reduction of the CBZ protected hydroxyproline to the corresponding 2-hydroxymethyl pyrrolidine, the CBZ protecting group is easily removed utilizing a palladium on charcoal reduction under a balloon of hydrogen. This reaction proceeds smoothly giving a quantitative yield of (2S, 4R)-4-hydroxy-2-hydroxy-methylpyrrolidine.

Attachment of the lipophilic tail compound of interest, such as cholesterol, to the linking molecule is done completely independent of any oligonucleotide synthesis. The low molecular weight tail molecule of interest, such as cholesterol, is attached to the linking molecule utilizing organic chemistry techniques and reactions. The secondary amino group of linking molecule is utilized to link the low molecular weight tail molecule of interest to the linking molecule, e.g. (2S, 4R)-4-hydroxy-2-hydroxymethylpyrrolidine, via any one of a number of suitable connections or linkage, as for instance an amide linkage, a carbonate linkage, an urea linkage, a thiourea linkage, or a sulfonamide linkage.

After the lipophilic moiety of interest, which eventually will be at the 3' tail of the oligonucleotide, is connected to the linking molecule (linker), the primary hydroxyl group on the linking molecule is appropriately protected, as for instance with a dimethoxytrityl group. This is conveniently accomplished utilizing dimethoxytritylchoride (DMTrCl) in pyridine in the presence of 4-dimethylaminopyridine (DMAP). This selectively protects the primary alcohol of the linking molecule. The secondary alcohol of the linking molecule is then converted to a succinate ester utilizing succinic anhydride. The succinate ester of the linking molecule (protected with DMTr on the primary hydroxyl group) bearing the low molecular weight compound of interest thereon can be coupled to a controlled pore glass support utilizing the older p-nitrophenol-DCC method of Atkinson, et al. in "Oligonucleotide Synthesis: A Practical Approach", M. J. Gait, Ed., IRL Press, p. 35–81 (1984). Preferably however the method of Gamper et al., Nucleic Acids Research, 1993, Vol. 21, No. 1 p 145–150 is employed. In this method the tail molecule (e. q. cholesterol) linked to the linker (e, g. (2S, 4R)-4-hydroxy-2-hydroxymethylpyrrolidine) which is in turn had been reacted with succinic anhydride, is reacted with 2,3,5,6-tetrafluorophenyl trifluoroacetate to provide the corresponding tetrafluorophenyl ester. The latter is an "activated" ester and reacts with LCAA-CPG (long chain alkylamine controlled pore glass) in the presence of triethylamine to provide the tail molecule attached (through the linker) to the controlled pore glass support (CPG). For further detailed description of this preferred method reference is made to the experimental provided below and to the Gamper et al., article which is incorporated herein by reference.

Controlled pore glass supports derivatized with long chain alkylamines (LCAA-CPG) are available from Pierce Chemical or from Sigma Chemical. After attachment of the linking molecule to the solid state support, excess long chain alkylamino groups on the support are capped by acetylating the same with acetic anhydride.

The dimethoxytrityl group is removed from the primary alcohol of the linking molecule by treating with 3% dichloroacetic acid in dichloromethane. The resulting controlled pore glass support, having the low molecular weight tail molecule attached thereto via the linking molecule (and with the primary hydroxyl group of the linking molecule now deblocked), is now ready for synthesis of the oligonucleotide thereon. It should be recognized that the solid state support loaded with the linking molecule and the with the lipophilic moiety of interest can also be prepared in bulk and then subdivided for the synthesis of multiple oligonucleotides, or can be stored for later use. In any event, oligonucleotide synthesis is initiated from the primary hydroxyl group of the linking molecule using phosphoramidite chemistry on a DNA synthesizer, as for instance a Milligen DNA synthesizer, in a normal manner.

Once synthesis of the oligonucleotide is complete, the oligonucleotide is deprotected in the standard manner for oligonucleotides synthesized on automated DNA synthesizers. The oligonucleotide with the low molecular tail molecule joined to its 3' terminus via the linking molecule is then cleaved from the solid state support also in the normal manner for automated DNA synthesis utilizing concentrated ammonia at room temperature in the normal manner.

Usually only a single purification step is necessary to purify the oligonucleotide having the low molecular weight tail molecule joined to its 3' terminus via the linking molecule. This can conveniently be done utilizing reverse phase HPLC chromatography.

Referring back now to FIG. 11, 3'-modifier (tail) groups tested in connection with the present invention include the acridinyl moiety, the hexadecyl moiety and various steroid-like lipophilic moieties. As the activity data provided in FIG. 10 indicate however, ODNs containing the acridinyl, or hexadecyl moiety as the lipophile, as well as certain steroid like lipophiles are not active, and not within the scope of the present invention. Under the heading "sterol supports" FIG. 11 discloses the structures of specific exemplary solid phase supports attached to specific exemplary steroid molecules through the presently preferred linking moiety derived from 2-hydroxymethyl-4-hydroxypyrrolidine.

Referring now to the table of FIG. 10, the activity of certain oligonucleotides in the HepG2 CMC assay, is disclosed. These ODNs have the sequence of ODN 128 (see FIG. 4) and the 3'-tail structures shown in FIG. 11. As it can be seen, the ODNs having "steroid-type" lipophilic tails are active where attachment of the steroid is through the A ring of the steroid. Generally speaking, the scope of the present invention extends to ODNs which otherwise meet the above-described structural requirements and where the steroidal moiety attached to the 3'-phosphate tail has the general structure shown in Formula 1.

The 5' end of the ODNs of the present invention preferably has the free primary hydroxyl group of the terminal deoxyribonucleotide, or terminates with a phosphate group. However, various other groups, such as phosphorothioate, as well as lipophilic groups, can be attached to the 5' end with or without a linker group within the scope of the invention. The table of FIG. 13 illustrates the structures of several exemplary ODNs within the scope of the invention and indicates their activity in the HepG2 CMC assay. As it can be seen, one example is a hexylamine tail attached to the 5'-phosphate end of the ODN, another example is a hexanol tail attached in the same manner. The six ODNs shown in FIG. 13 have the sequence of ODN 128, and also have the "cholesterol tail" at the 3'-end, as shown in Formula 3. Generally speaking, ODNs are within the scope of the present invention which otherwise meet the above-described structural requirements and have no 5'-tail, or have the 5'-tail shown and defined in connection with Formula 2.

Referring now back to FIG. 1, Type 3 ODNs within the scope of the present invention have regions which are complementary to one another, and also a region which is capable of forming a "hairpin turn" so as to allow duplex formation within the molecule. As is known, a region of three to eight nucleotides, preferably three to four nucleotides, such as for example a region incorporating three or four thymidylic acid residues (TTTT), allows the formation of a hairpin turn. Such modified ODNs are also within the scope of the invention where the region of the hairpin turn is other than an oligonucleotide segment. Examples for suitable groups (other than nucleotides) to form regions for the hairpin turn are alkylene groups [—(CH$_2$)$_p$—], groups derived from polyglycols, and polyglycols also containing an amine functionality, —(O—CH$_2$CH$_2$)$_p$— and (O—CH$_2$CH$_2$)$_q$—NH—CH$_2$CH$_2$—(O—CH$_2$CH$_2$)$_r$ where the symbols p, q and r are as defined above. The hairpin turn region may include more than one amine functionality. In general terms the hairpin turn region is a covalent chain of such length which allows the approximately 7 to 18 nucleotide long complementary regions of the oligonucleotide to hybridize with Watson-Crick type base pairing. Generally speaking a covalently bonded chain (other than oligonucleotides) of approximately 6 to 30 atoms allows the formation of a hairpin turn. A lipophilic tail, such as the cholesterol tail shown by Formula 3 (without the 5-hydroxymethyl 3-pyrrolidinol linker) can also be attached to the amine functionality. In such a case the Type 3 oligonucleotide mimicks the Type 1 and Type 2 oligonucleotides of the invention in that this modified Type 3 ODN also has a lipophilic tail at each "end" of the molecule.

FIG. 14 illustrates the structure and activity of exemplary Type 3 ODNs within the scope of the invention. As it can be seen, ODNs with a nucleotide (GAAA or TTTT) hairpin region as well as with non-nucleotide hairpin region are active. The ODN 210H is particularly noteworthy because it includes within the hairpin loop a 5-hydroxymethyl-2-pyrrolidinol moiety to which the "cholesterol tail" like structure is attached. ODNs 211H and 212H are inactive and outside of the scope of the invention because they do not form substantially stable duplexes.

Anticancer activity of the ODNs of the present invention was also confirmed in animal experiments. Mice injected intra peritoneally with adriamycin senitive P388-S leukemic cells, and also mice injected intra peritoneally with adriamycin resistant P388-R leukemic cells were treated (intraperitonially) with varying concentrations of ODN 128H (structure shown in FIG. 4). As is shown in the table below, significant increase in lifespan (ILS) was observed as a result of treatment.

TABLE 1

EFFECT OF COMPOUNDS ON SURVIVAL TIME OF MICE BEARING LEUKEMIA CELLS

| GROUP | NO. of MICE | DOSE (mg/kg) | Route Injection | SURV DAYS | ILS[b] (%) | DEATH TIME (day) |
|---|---|---|---|---|---|---|
| P388-S CONTROL | 6 | | | 13.3 | | 11,12,13 13,13,18 |
| 128H | 6 | 5 × 3 × 5 | I.P | 16.8 | 26 | 15,16,16 17,18,19 |
| | 6 | 2 × 3 × 5 | I.P | 20.7 | 55 | 11,15,17 21,25,35 |
| P388-R CONTROL | 6 | | | 11.0 | | 10,10,10 11,12,13 |
| 128H | 6 | 5 × 3 × 5 | I.P | 14.7 | 33 | 12,12,13 13,18,20 |
| | 6 | 2 × 3 × 5 | I.P | 15.8 | 44 | 12,13,15 16,17,21 |

Inoculum: 10$^6$ P388-S or P388-R cells were inoculated into each mouse (i.p.)
[a]Treatment was given daily on days 1,2,3,4,5 at which the animals received injections of the drug (day of tumor inoculation is Day 0)
[b]ILS, Increase in life span over controls which is expressed in terms of dying mice Description of Biological Testing Methods, Specific Examples, Cell Lines and Culture Conditions A number of cell lines were screened for the effect of 3'-cholesterol modified ODNs with respect to cell morphological changes (CMC). A majority of these cell lines are available with the American Type Culture Collection. The rest of them were either originated in the laboratory or were gifts from researchers who generated them. The cell lines are mentioned below with their culture conditions in parentheses. They are broadly classified into 3 major categories:
1. Human cell lines
2. Mouse cell lines
3. Others
1. Human Cell Lines:
   HepG2(Minimal Essential Medium with Earl's salts with 10% fetal bovine serum), HepG2 2.2.15(Minimal Essential Medium with Earl's salts with 10% fetal bovine serum), LoVo-2(F-12 with 10% fetal bovine serum), SW 837 (Liebovitz L-15 medium with 10% fetal bovine serum), CaCo-2(Minimal Essential Medium with Earl's salts and 20% fetal bovine serum), HT-29(McCoy's medium with 10% fetal bovine serum), H-9(RPMI with 20% dialyzed fetal bovine serum), MT-2 (RPMI with 10% dialyzed fetal bovine serum), HL-60 (RPMI with 15% heat-inactivated fetal bovine serum)
2. Mouse Cell Lines:
   ML3 (Dulbecco's minimal essential medium, TIB 73 (Dulbecco's Minimal essential medium with 10% fetal bovine serum), TIB 74 (Dulbecco's Minimal essential Medium with 10% fetal bovine serum), TIB 75 (Dulbecco's Minimal essential medium with 10% fetal bovine serum), Colon-38(RPMI with 10% fetal bovine serum), 197 Hep (Minimal essential medium with Earl's salts with 10% fetal bovine serum and growth factors namely insulin, transferrin, hydrocortisone and epidermal growth factor)

3. Other Cell Lines:
   Vero (RPMI with 5% fetal bovine serum)
   Culture Conditions:
   The aforementioned cell lines were grown in their respective media and in 5% $CO_2$ conditions at 37° C. except in the case of cells grown in Liebovitz's L-15 medium in which case they were incubated under non-$CO_2$ conditions.

Cell Morphology Change (CMC) Assay

During the treatment, the regular fetal bovine serum in the medium was substituted with heat inactivated fetal bovine serum. Cells of 10,000 per well were plated in 24-well plate and grown in 0.5 ml of indicated medium for 24 hours. The cultures were then exposed to oligonucleotides at indicated concentrations. Cultures were examined for the cell morphological changes after 24 hours under phase contrast invertoscope (Reichert-Jung). The examination was extended to the subsequent three days. Cultures not treated with any oligonucleotides were also run in parallel as controls. In each case, duplicate treatments were conducted. Careful examination of the cultures were made to detect any cellular secretion, cell floating etc. CMC effects include vacuolization, enlarged cell shape, a certain degree of cell lysis, and "cloudy" cellular secretion.

Clonogenic Assay

HepG2 cells (500) were plated in 6-well-plates in Minimal essential medium with Earl's salts with 10% fetal bovine serum. After 24 hours, the cultures were treated with varying concentrations of ODNs. Control cultures received media change without any oligonucleotides. The cultures were incubated for 24 hours at which point the medium was aspirated, and the cells were maintained in the fresh medium. After 10 days, the cultures were fixed and stained with methylene blue. Macroscopic colonies were counted.

Cell Line Specificity of ODN 065H

A number of cell lines were screened for the effect of ODN 065H with respect to the cell morphological changes (CMC). The cells were treated with 10 μM concentrations of either ODN 065H or ODN 075H for 24 hours (see FIG. 3 for sequence data). The morphology of the cells was examined as described above. The results of the testing are presented in FIG. 2. ODN 075H was inactive in all of the cell lines.

Thermal Denaturation Studies

Thermal dissociation curves were obtained by following changes in $A_{260}$ of aqueous solutions containing equimolar amounts of the particular ODN and its complementary strand. ODNs were prepared as 3 μM solutions in pH 7.2 PBS (9.2 mM disodium phosphate, 0.8 mM monosodium phosphate, 0.131M sodium chloride). A Gilford System 2600 UV-VIS spectrophotometer equipped with a Gilford 2527 Thermo-programmer was used. The samples were heated from 15° C. to 85° C. with a temperature increase of 0.5° C. / min. Absorbance vs. time and the first derivative data were recorded automatically. The $T_m$ was determined using the derivative maxima.

Anti-tumor Testing in Mouse Model of P388 Leukemia cells

One million adriamycin sensitive and one million adriamycin resistant P388 leukemia cells were injected intra peritoneally into respective groups of mice, one day prior to commencement of treatment with ODN 128H. From day 1 to day 5, ODN 128H was given intra peritoneally to these tumor bearing mice three times a day, in doses of 2 mg/kg and 5 mg/kg. Each group consisted of 5 mice. The effect of the treatment was evaluated by increase in life span over untreated controls.

Gel-Retardation Studies

One fifth volume of 5x gel-loading buffer (0.25% bromphenol blue, 0.25% xylene cyanol FF, 20% Ficoll in water) was added to each sample of oligonucleotide ($5 \times 10^{-5}$M in TE buffer, pH 7.5). All the samples were heated for 2 min at 95° C. and then allowed to cool at 4° C. The 2 μl aliquots were loaded on the 15% polyacrylamide gel (160×160×0.4 mm) which was preequilibrated at 4° C. 100 mM trisacetate, pH 7.2, containing 1 mM EDTA, was used as an electrode buffer for gel runing. Gel was run at 4° C., 150 V during the time which is necessary for bromphenol blue to run approximately 10 cm. The gel was fixed and stained according to the recomendations supplemented to the Silver Stain Kit "DAIICHI" (Daiichi Pure Chemicals Co., Ltd, Japan). The gel was dried on Whatman 3MM paper and photographed.

Synthesis and Purification of Modified Oligonucleotides

Modified ODNs were prepared from 2 μmole of the appropriate CPG support on an Applied Biosystems Model 380B or Model 394 using the 1 μmole synthesis DNA protocols supplied by the manufacturer. Modified RNA or 2'-O-Methyl oligonucleotides were prepared using RNA coupling cycle protocols. Standard reagents for β-cyanoethylphosphoramidite coupling chemistry were purchased from Glen Research. Phosphorothioate ODNs were prepared using 3H-1,2-benzodithiole-3-one 1,1 dioxide as the sulfurizing agent. 5'-modifications were introduced on the synthesizer using appropriate phosphoramidites. N-MMT-hexanolamine phosphoramidite was purchased from Milligen.

ODNs were deprotected in aqueous ammonia, HPLC purified on a Hamilton PRP-1 column and detritylated with 80% acetic acid for 1 hour. After butanol precipitation, the ODN pellet was reconstituted with 1 mL of water and concentration was determined. All ODN concentrations were determined in Tris buffer (0.1M, pH 7.5) at 260 nm. Extinction coefficients at 260 nm were calculated using a nearest neighbor model (Cantor, C. R., Warshaw, M. M. and Shapiro, H. (1970) Biopolymers 9: 1059–1077) (c) correcting for the molecular weight and UV absorbance of appended modifications. Residual triethylammonium salts were removed from the ODN by drying with excess sodium bicarbonate. The solid residue was reconstituted with 1 mL of water, filtered through a 0.2 μm filter, and concentration was redetermined. The purified ODNs were analyzed by HPLC on a Rainin Dynamax C18 column (0.75×25 cm) using a linear gradient of 5% –85% acetonitrile in 0.1M TEAA over 40 minutes (flow rate =1 mL/min). Unless otherwise noted, modified ODNs were greater than 90% pure by HPLC and one major band by PAGE. ODNs which were less than 90% pure by C18 HPLC were re-purified by HPLC on a 10×250 mm semiprep C18 column (same gradient). ODN purity was confirmed by polyacrylamide gel electrophoresis (20% polyacrylamide-7M urea). The nucleotidic bands were stained with either methylene blue or silver stain. All modified oligonucleotides gave one major band by PAGE.

ODN 089H, ODN 099H, and ODN 128H for animal studies were prepared on a 15 μmole scale using an ABI 394 synthesizer (10 μmole coupling cycle). After deprotection, the ammonia solution was purified by HPLC on a 22×175 mm PRP-1 column. After detritylation and precipitation, the product was further purified by HPLC on a 21×250 mm preparative C18 column. Triethylammonium salts were removed from the ODN by drying with excess sodium bicarbonate (confirmed by $^1$NMR analysis). The solid residue was reconstituted with 3 mL of water and concentration was redetermined. The purified ODNs were at least 98% pure by analytical C-18 HPLC. A single 15 μmole synthesis yielded ~25 mg of pure ODN (based on a calculated extinction coefficient). Several synthetic runs were combined and excess sodium bicarbonate was removed by ultrafiltration through a 3000 MW cutoff membrane (10 mL stirred cell). After 3 concentrations from 10 mL to 1 mL, the retentate was transferred to a 10 mL polypropylene tube and dried to constant weight.

DETAILED EXPERIMENTAL PROCEDURES

General Chemical Procedures.

All air- or water-sensitive reactions were carried out in oven dried glassware under a slight positive pressure of argon. Anhydrous solvents were obtained from Aldrich (Milwaukee, Wis.). THF was distilled from sodium and benzophenone. Removal of solvents at 15–30 Torr was accomplished on a rotary evaporator. Melting points were determined in an open glass capillary tube using a Mel-Temp (Cambridge, Mass.) melting point apparatus and are uncorrected. Infrared spectra were obtained with a Perkin-Elmer 783 spectrophotometer using the 1601 $cm^{-1}$ absorption of polystyrene as a standard reference. UV spectra were obtained with a Beckman (Fullerton, Calif.) DU-40 spectrophotometer using 0.1 mL quartz cuvettes. Proton magnetic resonance spectra were recorded using a Varian Gemini FT-200 (200 MHz) spectrometer. Appropriate solvent resonances were consistently used as internal references. All chemical shifts are reported in ppm downfield from tetramethylsilane. Elemental analyses were performed by Quantitative Technologies, Inc. (Bound Brook, N.J.). Flash chromatography was performed with EM Science (Cherry Hill, N.J.) silica gel 60 (230–400 mesh). Analytical thin layer chromatography was carried out on EM Science $F_{254}$ aluminum backed, fluorescence indicator plates. Plates were visualized with UV light, unless otherwise indicated. Unless otherwise stated, yields refer to isolated compounds of greater than 95% purity, as determined by $^1H$ NMR spectroscopy.

1-Benzyloxycarbonyl-5-hydroxymethyl-(3R-trans)-pyrrolidinol (1).

To an ice cold solution of 4.76 g (18 mmol) of N-Cbz-hydroxy-L-proline (Sigma Chemical Co.) in 20 mL of dry THF was added 45 mL of a 1M solution of borane. THF complex in THF (Aldrich). After stirring under argon for 15 min at 0°–5° C., and 4.5 h at room temperature, the mixture was cautiously quenched with 50 mL of methanol. After 30 min, the solution was concentrated. The residual colorless syrup was purified by flash chromatography (3.5×23 cm silica) using a gradient of methanol in methylene chloride. The product 1 eluted with 10% methanol. The fractions containing pure product were evaporated to dryness to give 2.18 g (46% yield) of 1 as a colorless syrup: TLC (95:5-methylene chloride:methanol), $R_f$=0.16; IR (neat) 3600–3100 (br), 2940, 1680, 1420 and 1355 $cm^{-1}$; $^1H$ NMR (CDCL$_3$) 7.36 (s, 5H), 5.17 (s, 2H), 4.50 (m, 2H), 3.67 (m, 4H), 2.09 (m, 3H). Anal. Calcd for $C_{13}H_{17}NO_4 \cdot 0.3H_2O$: C, 60.83; H, 6.91; N, 5.46. Found: C, 60.85; H, 6.88; N, 5.36.

5-Hydroxymethyl-(3R-trans)-pyrrolidinol (2).

A solution of 1.92 g (7.6 mmol) of the Cbz-protected aminodiol 1 in 50 mL of methanol was stirred with 320 mg of 10% Pd on carbon under a balloon of hydrogen. After 16 h no starting material remained as evidenced by TLC (9:1-methylene chloride:methanol). The mixture was filtered through diatomaceous earth (washed with methanol), and the filtrate was concentrated to give the product 2 as an amber syrup in quantitative yield. The syrup was dissolved in ethanol to give 15.2 mL of a 0.5M stock solution. TLC (3:1:1:1-ethyl acetate:acetone:methanol:water), $R_f$=0.06, pink spot with ninhydrin spray; IR (neat) 3600–3100 (br), 2920, 1530 and 1410 $cm^{-1}$; $^1H$ NMR (D$_2$O) 4.40 (m, 1H), 3.60 (m, 3H), 3.02 (d of d, 1H, J=12.4, 4.8 Hz), 2.77 (d of t, 1H, J=12.4, 1.8 Hz), 1.84 (m, 1H), 1.60 (m, 1H).

1-Cholesteryloxycarbonyl-5-hydroxymethyl-(3R-trans)-pyrrolidinol (3).

To 7.6 mL (3.8 mmol) of a 0.5M stock solution of the aminodiol 2 in ethanol was added a solution of 1.48 g (3.3 mmol) of cholesterol chloroformate in 8 mL of methylene chloride. The solution was stirred at room temperature for 1.5 h. The cloudy solution was poured into 100 mL of ice water and the heterogeneous mixture was extracted with 3×150 mL of hot ethyl acetate. The combined organics were washed with brine, dried over magnesium sulfate and concentrated. The solid residue was purified by flash chromatography (4×15 cm silica) using a gradient of methanol in 1:1-hexanes:ethyl acetate. The product 3 eluted with 10% methanol. The fractions containing pure product were evaporated to dryness to give 1.42 g (81% yield) of 3 as a white solid: TLC (45:45:10-hexanes:ethyl acetate:methanol), $R_f$=0.11, stained black upon charring with 10% sulfuric acid in methanol; $^1H$ NMR (CDCl$_3$) 5.38 (d, 1H), 4.85–4.00 (m, 3H), 3.90–3.30 (m, 4H), 2.50–2.15 (m, 2H), 2.15–0.60 (m, 43H). Anal. Calcd for $C_{33}H_{55}NO_4$: C, 74.81; H, 10.46; N, 2.64. Found: C, 74.74; H, 10.33; N, 2.50.

A mixture of 1 mg of 3 in 1 mL of 30% ammonium hydroxide was heated at 45° C. for 24 h in a sealed vial (ODN deprotection conditions). The resulting heterogeneous mixture was analyzed by TLC. Neither the solution or the solid showed any signs of decomposition.

1-Cholesteryloxycarbonyl-5-[bis(4-methoxyphenyl) phenylmethoxy]methyl-(3R-trans)-pyrrolidinol (4).

To a stirred solution of 1.42 g (2.68 mmol) of the diol 3 in 27 mL of dry pyridine was added 0.524 mL of triethylamine, 16.5 mg of DMAP, and 1.10 g (3.23 mmol) of DMTr chloride. After stirring under argon for 4.5 h, the mixture was stripped of solvent. Residual pyridine was removed by co-evaporation with toluene. The residue was partitioned between 100 mL of ether and 40 mL of water. The aqueous layer was extracted with 80 mL of ether and the combined organic layers were washed with brine, dried over sodium sulfate, and concentrated. The residue was purified by flash chromatography (4.5×20 cm silica) using a gradient of ethyl acetate in hexanes. The product eluted just after a yellow impurity using 2:1-hexanes:ethyl acetate. The fractions containing pure product were evaporated to dryness to give 1.33 g (60% yield) of 4 as a pale yellow solid foam: TLC (95:5-methylene chloride:methanol), $R_f$=0.49, stained orange upon spraying with 10% sulfuric acid in methanol; $^1H$ NMR (CDCl$_3$) 7.26 (m, 9H), 6.81 (d, 4H, J=8.8 Hz), 5.30 (m, 1H), 4.50 (m, 2H), 4.15 (m, 1H), 3.78 (s, 6H), 3.7–3.0 (m, 4H), 2.4–0.6 (m, 46H). Anal. Calcd for $C_{54}H_{73}NO_6$: C, 77.94; H, 8.84; N, 1.68. Found: C, 77.26; H, 8.82; N, 1.56.

Succinate Intermediate (5).

To a stirred solution of 1.22 g (1.47 mmol) of the alcohol 4 in 12 mL of dry pyridine was added 443 mg (4.43 mmol) of succinic anhydride and 89 mg (0.73 mmol) of DMAP. The mixture was stirred under argon for 26 h and evaporated to dryness. Residual pyridine was removed by co-evaporation with toluene. The residue was dissolved in 40 mL of chloroform, washed with brine, dried over sodium sulfate and concentrated to give quantitative yield of the succinylated product as a beige solid foam: TLC (95:5-methylene chloride:methanol), $R_f$=0.32, stained orange upon spraying with 10% sulfuric acid in methanol.

2,3,5,6-Tetrafluorophenyl trifluoroacetate (6).

A mixture of 2,3,5,6-tetrafluorophenol (55.2 g, 0.33 mol), trifluoroacetic anhydride (60 mL, 0.42 mol) and boron trifluoride etherate (0.5 mL) was refluxed for 16 hr. Trifluoroacetic anhydride and trifluoroacetic acid were removed by distillation at atmospheric pressure. The trifluoroacetic anhydride fraction (bp 40° C.) was returned to the reaction mixture along with 0.5 mL of boron trifluoride etherate, and the mixture was refluxed for 24 hr. This process was repeated two times to ensure complete reaction. After distillation at atmospheric pressure, the desired product (6) was collected at 62° C./45 mm (45° C./18 mm) as a colorless liquid: yield =81.3 g (93%); d=1.52 g/mL; $n_D^{21}$=1.3747; IR (CHCl$_3$) 3010, 1815, 1525, 1485, 1235, 1180, 1110, and 955 cm$^{-1}$. Anal. Calcd for $C_8HF_7O_2$: C, 36.66; H, 0.38; F, 50.74. Found: C, 36.31; H, 0.43; F, 50.95.

2,3,5,6-Tetrafluorophenyl 1-[(cholesteryloxy)carbonyl]-5-[ [bis(4-methoxyphenyl )phenylmethoxy]methyl ]-(3R-trans)-pyrrolidinylbutanedioate (7).

The carboxylic acid (5) was prepared as described above and purified by flash chromatography over silica gel (elution with 95:5:5 methylene chloride-methanol-triethylamine). To an ice-cold solution of the purified product (1.93 g, 1.86 mmol) in 25 mL of dry methylene chloride was added 520 μl (3.72 mmol) of triethylamine. A solution of 469 μl (2.76 mmol) of 2,3,5,6-tetrafluorophenyl trifluoroacetate (6) in 3 mL of dry methylene chloride was added dropwise with stirring. TLC showed complete reaction of starting acid in less than one h. The reaction mixture was concentrated and the residue was purified by flash chromatography (3.5×20 cm silica) using hexanes-ethyl acetate. The fractions containing pure product were evaporated to give 1.62 g (81% yield) of the TFP ester 7 as a white solid foam: TLC (2:1 hexanes-ethyl acetate) $R_f$=0.66, stained orange upon spraying with 10% sulfuric acid in methanol. $^1$H NMR (CDCl$_3$) δ 7.26 (m, 9H), 7.00 (m, 1H), 6.82 (d, 4H, J =8.6 Hz), 5.42 (m, 1H), 5.30 (m, 1H), 4.13 (m, 1H), 3.78 (s, 6H), 3.7–2.9 (m, 6H), 2.77 (t, 2H, J=6.8 Hz), 2.4–0.6 (m, 46H). Anal. Calcd for $C_{64}H_{77}F_4NO_9$ (4% free TFP): C, 70.04; H, 6.94; N, 1.25; F, 8.68. Found: C, 70.02; H, 6.97; N, 1.17; F, 8.55.

Cholesterol-CPG (8).

A mixture of 2.70 g of LCAA-CPG, 470 μl of diisopropylethylamine, and 292 mg (0.27 mmol) of the TFP ester (7) in 13.5 mL of dry dimethylformamide were swirled in a 50 mL round bottomed flask (orbital mixer, 150 rpm). After 49 hr, the CPG was filtered on a sintered glass funnel (medium porosity) and washed with 50 mL portions of dimethylformamide, methanol, and diethyl ether. The CPG was dried under vacuum and treated with 14 mL of dry pyridine and 1.75 mL of acetic anhydride. After swirling 18 hr, the CPG was filtered and washed with pyridine, methanol and diethyl ether, then dried under vacuum. The product (8) was analyzed for dimethoxytrityl (DMTr) content and found to have a loading of 41 micromol/g.

SEQUENCE LISTING ( 1 ) GENERAL INFORMATION:

( i i i ) NUMBER OF SEQUENCES: 70

( 2 ) INFORMATION FOR SEQ ID NO:1:

( i ) SEQUENCE CHARACTERISTICS:
      ( A ) LENGTH: 14 base pairs
      ( B ) TYPE: nucleic acid
      ( C ) STRANDEDNESS: single
      ( D ) TOPOLOGY: linear ( i x ) FEATURE:
      ( A ) NAME/KEY: modified_base
      ( B ) LOCATION: 14
      ( D ) OTHER INFORMATION: /mod_base=OTHER
        / note="Nucleotide 14 has a tail which comprises
        a cholesterol moiety which has its A ring linked to
        the 3'- phosphate through a carbonyl group attached
        to the ring nitrogen of a moiety derived from
        4-hydroxy-2- hydroxymethylpyrrolidine (see
        formula 3)."

( x i ) SEQUENCE DESCRIPTION: SEQ ID NO:1:

GACACACGGG TGAT                                            14

( 2 ) INFORMATION FOR SEQ ID NO:2:

( i ) SEQUENCE CHARACTERISTICS:
    ( A ) LENGTH: 14 base pairs
    ( B ) TYPE: nucleic acid
    ( C ) STRANDEDNESS: single
    ( D ) TOPOLOGY: linear ( i x ) FEATURE:
    ( A ) NAME/KEY: modified_base
    ( B ) LOCATION: 14
    ( D ) OTHER INFORMATION: /mod_base=OTHER
        / note="Nucleotide 14 has a tail which comprises
        a cholesterol moiety which has its A ring linked to
        the 3'- phosphate through a carbonyl group attached
        to the ring nitrogen of a moiety derived from
        4-hydroxy-2- hydroxymethylpyrrolidine (see
        formula 3)."

( x i ) SEQUENCE DESCRIPTION: SEQ ID NO:2:

GACACACGGT TGAT                                        14

( 2 ) INFORMATION FOR SEQ ID NO:3:

( i ) SEQUENCE CHARACTERISTICS:
    ( A ) LENGTH: 12 base pairs
    ( B ) TYPE: nucleic acid
    ( C ) STRANDEDNESS: single
    ( D ) TOPOLOGY: linear ( i x ) FEATURE:
    ( A ) NAME/KEY: modified_base
    ( B ) LOCATION: 12
    ( D ) OTHER INFORMATION: /mod_base=OTHER
        / note="Nucleotide 12 has a tail which comprises
        a cholesterol moiety which has its A ring linked to
        the 3'- phosphate through a carbonyl group attached
        to the ring nitrogen of a moiety derived from
        4-hydroxy-2- hydroxymethylpyrrolidine (see
        formula 3)."

( x i ) SEQUENCE DESCRIPTION: SEQ ID NO:3:

CACACGGGTG AT                                          12

( 2 ) INFORMATION FOR SEQ ID NO:4:

( i ) SEQUENCE CHARACTERISTICS:
    ( A ) LENGTH: 11 base pairs
    ( B ) TYPE: nucleic acid
    ( C ) STRANDEDNESS: single
    ( D ) TOPOLOGY: linear ( i x ) FEATURE:
    ( A ) NAME/KEY: modified_base
    ( B ) LOCATION: 11
    ( D ) OTHER INFORMATION: /mod_base=OTHER
        / note="Nucleotide 11 has a tail which comprises
        a cholesterol moiety which has its A ring linked to
        the 3'- phosphate through a carbonyl group attached
        to the ring nitrogen of a moiety derived from
        4-hydroxy-2- hydroxymethylpyrrolidine (see
        formula 3)."

( x i ) SEQUENCE DESCRIPTION: SEQ ID NO:4:

CACACGGGTG A                                             11

( 2 ) INFORMATION FOR SEQ ID NO:5:

( i ) SEQUENCE CHARACTERISTICS:
    ( A ) LENGTH: 10 base pairs
    ( B ) TYPE: nucleic acid
    ( C ) STRANDEDNESS: single
    ( D ) TOPOLOGY: linear ( i x ) FEATURE:
    ( A ) NAME/KEY: modified_base (B) LOCATION: 10
(D) OTHER INFORMATION: /mod_base=OTHER
/ note="Nucleotide 10 has a tail which comprises
a cholesterol moiety which has its A ring linked to
the 3'- phosphate through a carbonyl group attached
to the ring nitrogen of a moiety derived from
4-hydroxy-2- hydroxymethylpyrrolidine (see
formula 3)."

(xi) SEQUENCE DESCRIPTION: SEQ ID NO:5:

CACACGGGTG                                                                                    10

(2) INFORMATION FOR SEQ ID NO:6:

(i) SEQUENCE CHARACTERISTICS:
    (A) LENGTH: 11 base pairs
    (B) TYPE: nucleic acid
    (C) STRANDEDNESS: single
    (D) TOPOLOGY: linear (ii) MOLECULE TYPE: DNA (genomic)

(ix) FEATURE:
    (A) NAME/KEY: modified_base
    (B) LOCATION: 11
    (D) OTHER INFORMATION: /mod_base=OTHER
        / note="Nucleotide 11 has a tail which comprises
        a cholesterol moiety which has its A ring linked to
        the 3'- phosphate through a carbonyl group attached
        to the ring nitrogen of a moiety derived from
        4-hydroxy-2- hydroxymethylpyrrolidine (see
        formula 3)."

(xi) SEQUENCE DESCRIPTION: SEQ ID NO:6:

ACACGGGTGA T                                                                                  11

(2) INFORMATION FOR SEQ ID NO:7:

(i) SEQUENCE CHARACTERISTICS:
    (A) LENGTH: 10 base pairs
    (B) TYPE: nucleic acid
    (C) STRANDEDNESS: single
    (D) TOPOLOGY: linear (ix) FEATURE:
    (A) NAME/KEY: modified_base
    (B) LOCATION: 10
    (D) OTHER INFORMATION: /mod_base=OTHER
        / note="Nucleotide 10 has a tail which comprises
        a cholesterol moiety which has its A ring linked to
        the 3'- phosphate through a carbonyl group attached
        to the ring nitrogen of a moiety derived from
        4-hydroxy-2- hydroxymethylpyrrolidine (see
        formula 3)."

(xi) SEQUENCE DESCRIPTION: SEQ ID NO:7:

CACGGGTGAT                                                                                    10

(2) INFORMATION FOR SEQ ID NO:8:

(i) SEQUENCE CHARACTERISTICS:
    (A) LENGTH: 10 base pairs
    (B) TYPE: nucleic acid
    (C) STRANDEDNESS: single
    (D) TOPOLOGY: linear (ix) FEATURE:
    (A) NAME/KEY: modified_base
    (B) LOCATION: 10
    (D) OTHER INFORMATION: /mod_base=OTHER
        / note="Nucleotide 10 has a tail which comprises
        a cholesterol moiety which has its A ring linked to
        the 3'- phosphate through a carbonyl group attached
        to the ring nitrogen of a moiety derived from 4-hydroxy-2- hydroxymethylpyrrolidine (see
formula 3)."

( x i ) SEQUENCE DESCRIPTION: SEQ ID NO:8:

CACACGGGTA                                                                                                                10

( 2 ) INFORMATION FOR SEQ ID NO:9:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i x ) FEATURE:
        ( A ) NAME/KEY: modified_base
        ( B ) LOCATION: 10
        ( D ) OTHER INFORMATION: /mod_base=OTHER
        / note="Nucleotide 10 has a tail which comprises
        a cholesterol moiety which has its A ring linked to
        the 3'- phosphate through a carbonyl group attached
        to the ring nitrogen of a moiety derived from
        4-hydroxy-2- hydroxymethylpyrrolidine (see
        formula 3)."

( x i ) SEQUENCE DESCRIPTION: SEQ ID NO:9:

CACACGGGTC                                                                                                                10

( 2 ) INFORMATION FOR SEQ ID NO:10:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i x ) FEATURE:
        ( A ) NAME/KEY: modified_base
        ( B ) LOCATION: 10
        ( D ) OTHER INFORMATION: /mod_base=OTHER
        / note="Nucleotide 10 has a tail which comprises
        a cholesterol moiety which has its A ring linked to
        the 3'- phosphate through a carbonyl group attached
        to the ring nitrogen of a moiety derived from
        4-hydroxy-2- hydroxymethylpyrrolidine (see
        formula 3)."

( x i ) SEQUENCE DESCRIPTION: SEQ ID NO:10:

CACACGGGTT                                                                                                                10

( 2 ) INFORMATION FOR SEQ ID NO:11:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i x ) FEATURE:
        ( A ) NAME/KEY: modified_base
        ( B ) LOCATION: 10
        ( D ) OTHER INFORMATION: /mod_base=OTHER
        / note="Nucleotide 10 has a tail which comprises
        a cholesterol moiety which has its A ring linked to
        the 3'- phosphate through a carbonyl group attached
        to the ring nitrogen of a moiety derived from
        4-hydroxy-2- hydroxymethylpyrrolidine (see
        formula 3)."

( x i ) SEQUENCE DESCRIPTION: SEQ ID NO:11:

AACACGGGTG                                                                                                                10

( 2 ) INFORMATION FOR SEQ ID NO:12:

( i ) SEQUENCE CHARACTERISTICS:
    ( A ) LENGTH: 10 base pairs
    ( B ) TYPE: nucleic acid
    ( C ) STRANDEDNESS: single
    ( D ) TOPOLOGY: linear ( i x ) FEATURE:
    ( A ) NAME/KEY: modified_base
    ( B ) LOCATION: 10
    ( D ) OTHER INFORMATION: /mod_base=OTHER
      / note="Nucleotide 10 has a tail which comprises
      a cholesterol moiety which has its A ring linked to
      the 3'- phosphate through a carbonyl group attached
      to the ring nitrogen of a moiety derived from
      4-hydroxy-2- hydroxymethylpyrrolidine (see
      formula 3)."

( x i ) SEQUENCE DESCRIPTION: SEQ ID NO:12:

GACACGGGTG                                                                      10

( 2 ) INFORMATION FOR SEQ ID NO:13:

( i ) SEQUENCE CHARACTERISTICS:
    ( A ) LENGTH: 10 base pairs
    ( B ) TYPE: nucleic acid
    ( C ) STRANDEDNESS: single
    ( D ) TOPOLOGY: linear ( i x ) FEATURE:
    ( A ) NAME/KEY: modified_base
    ( B ) LOCATION: 10
    ( D ) OTHER INFORMATION: /mod_base=OTHER
      / note="Nucleotide 10 has a tail which comprises
      a cholesterol moiety which has its A ring linked to
      the 3'- phosphate through a carbonyl group attached
      to the ring nitrogen of a moiety derived from
      4-hydroxy-2- hydroxymethylpyrrolidine (see
      formula 3)."

( x i ) SEQUENCE DESCRIPTION: SEQ ID NO:13:

TACACGGGTG                                                                      10

( 2 ) INFORMATION FOR SEQ ID NO:14:

( i ) SEQUENCE CHARACTERISTICS:
    ( A ) LENGTH: 10 base pairs
    ( B ) TYPE: nucleic acid
    ( C ) STRANDEDNESS: single
    ( D ) TOPOLOGY: linear ( i x ) FEATURE:
    ( A ) NAME/KEY: modified_base
    ( B ) LOCATION: 10
    ( D ) OTHER INFORMATION: /mod_base=OTHER
      / note="Nucleotide 10 has a tail which comprises
      a cholesterol moiety which has its A ring linked to
      the 3'- phosphate through a carbonyl group attached
      to the ring nitrogen of a moiety derived from
      4-hydroxy-2- hydroxymethylpyrrolidine (see
      formula 3)."

( x i ) SEQUENCE DESCRIPTION: SEQ ID NO:14:

CACACGGGAG                                                                      10

( 2 ) INFORMATION FOR SEQ ID NO:15:

( i ) SEQUENCE CHARACTERISTICS:
    ( A ) LENGTH: 10 base pairs
    ( B ) TYPE: nucleic acid
    ( C ) STRANDEDNESS: single
    ( D ) TOPOLOGY: linear ( i x ) FEATURE:
    ( A ) NAME/KEY: modified_base
    ( B ) LOCATION: 10
    ( D ) OTHER INFORMATION: /mod_base=OTHER
        / note="Nucleotide 10 has a tail which comprises
        a cholesterol moiety which has its A ring linked to
        the 3'- phosphate through a carbonyl group attached
        to the ring nitrogen of a moiety derived from
        4-hydroxy-2- hydroxymethylpyrrolidine (see
        formula 3)."

( x i ) SEQUENCE DESCRIPTION: SEQ ID NO:15:

CACACGGGCG                                               10

( 2 ) INFORMATION FOR SEQ ID NO:16:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i x ) FEATURE:
        ( A ) NAME/KEY: modified_base
        ( B ) LOCATION: 10
        ( D ) OTHER INFORMATION: /mod_base=OTHER
            / note="Nucleotide 10 has a tail which comprises
            a cholesterol moiety which has its A ring linked to
            the 3'- phosphate through a carbonyl group attached
            to the ring nitrogen of a moiety derived from
            4-hydroxy-2- hydroxymethylpyrrolidine (see
            formula 3)."

( x i ) SEQUENCE DESCRIPTION: SEQ ID NO:16:

CACACGGGGG                                               10

( 2 ) INFORMATION FOR SEQ ID NO:17:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i x ) FEATURE:
        ( A ) NAME/KEY: modified_base
        ( B ) LOCATION: 10
        ( D ) OTHER INFORMATION: /mod_base=OTHER
            / note="Nucleotide 10 has a tail which comprises
            a cholesterol moiety which has its A ring linked to
            the 3'- phosphate through a carbonyl group attached
            to the ring nitrogen of a moiety derived from
            4-hydroxy-2- hydroxymethylpyrrolidine (see
            formula 3)."

( x i ) SEQUENCE DESCRIPTION: SEQ ID NO:17:

CACACAGGTG                                               10

( 2 ) INFORMATION FOR SEQ ID NO:18:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i x ) FEATURE:
        ( A ) NAME/KEY: modified_base
        ( B ) LOCATION: 10
        ( D ) OTHER INFORMATION: /mod_base=OTHER
            / note="Nucleotide 10 has a tail which comprises
            a cholesterol moiety which has its A ring linked to
            the 3'- phosphate through a carbonyl group attached
            to the ring nitrogen of a moiety derived from 4-hydroxy-2- hydroxymethylpyrrolidine (see
formula 3)."

( x i ) SEQUENCE DESCRIPTION: SEQ ID NO:18:

CACACCGGTG                                                                                                  10

( 2 ) INFORMATION FOR SEQ ID NO:19:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i x ) FEATURE:
        ( A ) NAME/KEY: modified_base
        ( B ) LOCATION: 10
        ( D ) OTHER INFORMATION: /mod_base=OTHER
          / note="Nucleotide 10 has a tail which comprises
          a cholesterol moiety which has its A ring linked to
          the 3'- phosphate through a carbonyl group attached
          to the ring nitrogen of a moiety derived from
          4-hydroxy-2- hydroxymethylpyrrolidine (see
          formula 3)."

( x i ) SEQUENCE DESCRIPTION: SEQ ID NO:19:

CACACTGGTG                                                                                                  10

( 2 ) INFORMATION FOR SEQ ID NO:20:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i x ) FEATURE:
        ( A ) NAME/KEY: modified_base
        ( B ) LOCATION: 10
        ( D ) OTHER INFORMATION: /mod_base=OTHER
          / note="Nucleotide 10 has a tail which comprises
          a cholesterol moiety which has its A ring linked to
          the 3'- phosphate through a carbonyl group attached
          to the ring nitrogen of a moiety derived from
          4-hydroxy-2- hydroxymethylpyrrolidine (see
          formula 3)."

( x i ) SEQUENCE DESCRIPTION: SEQ ID NO:20:

CCCACGGGTG                                                                                                  10

( 2 ) INFORMATION FOR SEQ ID NO:21:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i x ) FEATURE:
        ( A ) NAME/KEY: modified_base
        ( B ) LOCATION: 10
        ( D ) OTHER INFORMATION: /mod_base=OTHER
          / note="Nucleotide 10 has a tail which comprises
          a cholesterol moiety which has its A ring linked to
          the 3'- phosphate through a carbonyl group attached
          to the ring nitrogen of a moiety derived from
          4-hydroxy-2- hydroxymethylpyrrolidine (see
          formula 3)."

( x i ) SEQUENCE DESCRIPTION: SEQ ID NO:21:

CGCACGGGTG                                                                                                  10

( 2 ) INFORMATION FOR SEQ ID NO:22:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i x ) FEATURE:
        ( A ) NAME/KEY: modified_base
        ( B ) LOCATION: 10
        ( D ) OTHER INFORMATION: /mod_base=OTHER
        / note="Nucleotide 10 has a tail which comprises
        a cholesterol moiety which has its A ring linked to
        the 3'- phosphate through a carbonyl group attached
        to the ring nitrogen of a moiety derived from
        4-hydroxy-2- hydroxymethylpyrrolidine (see
        formula 3)."

( x i ) SEQUENCE DESCRIPTION: SEQ ID NO:22:

CTCACGGGTG        10

( 2 ) INFORMATION FOR SEQ ID NO:23:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i x ) FEATURE:
        ( A ) NAME/KEY: modified_base
        ( B ) LOCATION: 10
        ( D ) OTHER INFORMATION: /mod_base=OTHER
        / note="Nucleotide 10 has a tail which comprises
        a cholesterol moiety which has its A ring linked to
        the 3'- phosphate through a carbonyl group attached
        to the ring nitrogen of a moiety derived from
        4-hydroxy-2- hydroxymethylpyrrolidine (see
        formula 3)."

( x i ) SEQUENCE DESCRIPTION: SEQ ID NO:23:

CAAACGGGTG        10

( 2 ) INFORMATION FOR SEQ ID NO:24:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i x ) FEATURE:
        ( A ) NAME/KEY: modified_base
        ( B ) LOCATION: 10
        ( D ) OTHER INFORMATION: /mod_base=OTHER
        / note="Nucleotide 10 has a tail which comprises
        a cholesterol moiety which has its A ring linked to
        the 3'- phosphate through a carbonyl group attached
        to the ring nitrogen of a moiety derived from
        4-hydroxy-2- hydroxymethylpyrrolidine (see
        formula 3)."

( x i ) SEQUENCE DESCRIPTION: SEQ ID NO:24:

CAGACGGGTG        10

( 2 ) INFORMATION FOR SEQ ID NO:25:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i x ) FEATURE:
    ( A ) NAME/KEY: modified_base
    ( B ) LOCATION: 10
    ( D ) OTHER INFORMATION: /mod_base=OTHER
      / note="Nucleotide 10 has a tail which comprises
      a cholesterol moiety which has its A ring linked to
      the 3'- phosphate through a carbonyl group attached
      to the ring nitrogen of a moiety derived from
      4-hydroxy-2- hydroxymethylpyrrolidine (see
      formula 3)."

( x i ) SEQUENCE DESCRIPTION: SEQ ID NO:25:

CATACGGGTG    10

( 2 ) INFORMATION FOR SEQ ID NO:26:

( i ) SEQUENCE CHARACTERISTICS:
    ( A ) LENGTH: 10 base pairs
    ( B ) TYPE: nucleic acid
    ( C ) STRANDEDNESS: single
    ( D ) TOPOLOGY: linear ( i x ) FEATURE:
    ( A ) NAME/KEY: modified_base
    ( B ) LOCATION: 10
    ( D ) OTHER INFORMATION: /mod_base=OTHER
      / note="Nucleotide 10 has a tail which comprises
      a cholesterol moiety which has its A ring linked to
      the 3'- phosphate through a carbonyl group attached
      to the ring nitrogen of a moiety derived from
      4-hydroxy-2- hydroxymethylpyrrolidine (see
      formula 3)."

( x i ) SEQUENCE DESCRIPTION: SEQ ID NO:26:

CACCCGGGTG    10

( 2 ) INFORMATION FOR SEQ ID NO:27:

( i ) SEQUENCE CHARACTERISTICS:
    ( A ) LENGTH: 10 base pairs
    ( B ) TYPE: nucleic acid
    ( C ) STRANDEDNESS: single
    ( D ) TOPOLOGY: linear ( i x ) FEATURE:
    ( A ) NAME/KEY: modified_base
    ( B ) LOCATION: 10
    ( D ) OTHER INFORMATION: /mod_base=OTHER
      / note="Nucleotide 10 has a tail which comprises
      a cholesterol moiety which has its A ring linked to
      the 3'- phosphate through a carbonyl group attached
      to the ring nitrogen of a moiety derived from
      4-hydroxy-2- hydroxymethylpyrrolidine (see
      formula 3)."

( x i ) SEQUENCE DESCRIPTION: SEQ ID NO:27:

CACGCGGGTG    10

( 2 ) INFORMATION FOR SEQ ID NO:28:

( i ) SEQUENCE CHARACTERISTICS:
    ( A ) LENGTH: 10 base pairs
    ( B ) TYPE: nucleic acid
    ( C ) STRANDEDNESS: single
    ( D ) TOPOLOGY: linear ( i x ) FEATURE:
    ( A ) NAME/KEY: modified_base
    ( B ) LOCATION: 10
    ( D ) OTHER INFORMATION: /mod_base=OTHER
      / note="Nucleotide 10 has a tail which comprises
      a cholesterol moiety which has its A ring linked to
      the 3'- phosphate through a carbonyl group attached
      to the ring nitrogen of a moiety derived from 4-hydroxy-2- hydroxymethylpyrrolidine (see
formula 3)."

( x i ) SEQUENCE DESCRIPTION: SEQ ID NO:28:

CACTCGGGTG　　　　　　　　　　　　　　　　　　　　　　　　　　　　　10

( 2 ) INFORMATION FOR SEQ ID NO:29:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i x ) FEATURE:
        ( A ) NAME/KEY: modified_base
        ( B ) LOCATION: 10
        ( D ) OTHER INFORMATION: /mod_base=OTHER
        / note="Nucleotide 10 has a tail which comprises
        a cholesterol moiety which has its A ring linked to
        the 3'- phosphate through a carbonyl group attached
        to the ring nitrogen of a moiety derived from
        4-hydroxy-2- hydroxymethylpyrrolidine (see
        formula 3)."

( x i ) SEQUENCE DESCRIPTION: SEQ ID NO:29:

CACAAGGGTG　　　　　　　　　　　　　　　　　　　　　　　　　　　　　10

( 2 ) INFORMATION FOR SEQ ID NO:30:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i x ) FEATURE:
        ( A ) NAME/KEY: modified_base
        ( B ) LOCATION: 10
        ( D ) OTHER INFORMATION: /mod_base=OTHER
        / note="Nucleotide 10 has a tail which comprises
        a cholesterol moiety which has its A ring linked to
        the 3'- phosphate through a carbonyl group attached
        to the ring nitrogen of a moiety derived from
        4-hydroxy-2- hydroxymethylpyrrolidine (see
        formula 3)."

( x i ) SEQUENCE DESCRIPTION: SEQ ID NO:30:

CACAGGGGTG　　　　　　　　　　　　　　　　　　　　　　　　　　　　　10

( 2 ) INFORMATION FOR SEQ ID NO:31:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i x ) FEATURE:
        ( A ) NAME/KEY: modified_base
        ( B ) LOCATION: 10
        ( D ) OTHER INFORMATION: /mod_base=OTHER
        / note="Nucleotide 10 has a tail which comprises
        a cholesterol moiety which has its A ring linked to
        the 3'- phosphate through a carbonyl group attached
        to the ring nitrogen of a moiety derived from
        4-hydroxy-2- hydroxymethylpyrrolidine (see
        formula 3)."

( x i ) SEQUENCE DESCRIPTION: SEQ ID NO:31:

CACATGGGTG　　　　　　　　　　　　　　　　　　　　　　　　　　　　　10

( 2 ) INFORMATION FOR SEQ ID NO:32:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i x ) FEATURE:
        ( A ) NAME/KEY: modified_base
        ( B ) LOCATION: 10
        ( D ) OTHER INFORMATION: /mod_base=OTHER
            / note="Nucleotide 10 has a tail which comprises
            a cholesterol moiety which has its A ring linked to
            the 3'- phosphate through a carbonyl group attached
            to the ring nitrogen of a moiety derived from
            4-hydroxy-2- hydroxymethylpyrrolidine (see
            formula 3)."

( x i ) SEQUENCE DESCRIPTION: SEQ ID NO:32:

CACACGAGTG                10

( 2 ) INFORMATION FOR SEQ ID NO:33:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i x ) FEATURE:
        ( A ) NAME/KEY: modified_base
        ( B ) LOCATION: 10
        ( D ) OTHER INFORMATION: /mod_base=OTHER
            / note="Nucleotide 10 has a tail which comprises
            a cholesterol moiety which has its A ring linked to
            the 3'- phosphate through a carbonyl group attached
            to the ring nitrogen of a moiety derived from
            4-hydroxy-2- hydroxymethylpyrrolidine (see
            formula 3)."

( x i ) SEQUENCE DESCRIPTION: SEQ ID NO:33:

CACACGCGTG                10

( 2 ) INFORMATION FOR SEQ ID NO:34:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i x ) FEATURE:
        ( A ) NAME/KEY: modified_base
        ( B ) LOCATION: 10
        ( D ) OTHER INFORMATION: /mod_base=OTHER
            / note="Nucleotide 10 has a tail which comprises
            a cholesterol moiety which has its A ring linked to
            the 3'- phosphate through a carbonyl group attached
            to the ring nitrogen of a moiety derived from
            4-hydroxy-2- hydroxymethylpyrrolidine (see
            formula 3)."

( x i ) SEQUENCE DESCRIPTION: SEQ ID NO:34:

CACACGTGTG                10

( 2 ) INFORMATION FOR SEQ ID NO:35:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear -continued ( i x ) FEATURE:
    ( A ) NAME/KEY: modified_base
    ( B ) LOCATION: 10
    ( D ) OTHER INFORMATION: /mod_base=OTHER
        / note="Nucleotide 10 has a tail which comprises
        a cholesterol moiety which has its A ring linked to
        the 3'- phosphate through a carbonyl group attached
        to the ring nitrogen of a moiety derived from
        4-hydroxy-2- hydroxymethylpyrrolidine (see
        formula 3)."

( x i ) SEQUENCE DESCRIPTION: SEQ ID NO:35:

CACACGGATG         10

( 2 ) INFORMATION FOR SEQ ID NO:36:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i x ) FEATURE:
        ( A ) NAME/KEY: modified_base
        ( B ) LOCATION: 10
        ( D ) OTHER INFORMATION: /mod_base=OTHER
            / note="Nucleotide 10 has a tail which comprises
            a cholesterol moiety which has its A ring linked to
            the 3'- phosphate through a carbonyl group attached
            to the ring nitrogen of a moiety derived from
            4-hydroxy-2- hydroxymethylpyrrolidine (see
            formula 3)."

( x i ) SEQUENCE DESCRIPTION: SEQ ID NO:36:

CACACGGCTG         10

( 2 ) INFORMATION FOR SEQ ID NO:37:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i x ) FEATURE:
        ( A ) NAME/KEY: modified_base
        ( B ) LOCATION: 10
        ( D ) OTHER INFORMATION: /mod_base=OTHER
            / note="Nucleotide 10 has a tail which comprises
            a cholesterol moiety which has its A ring linked to
            the 3'- phosphate through a carbonyl group attached
            to the ring nitrogen of a moiety derived from
            4-hydroxy-2- hydroxymethylpyrrolidine (see
            formula 3)."

( x i ) SEQUENCE DESCRIPTION: SEQ ID NO:37:

CACACGGTTG         10

( 2 ) INFORMATION FOR SEQ ID NO:38:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i x ) FEATURE:
        ( A ) NAME/KEY: modified_base
        ( B ) LOCATION: 10
        ( D ) OTHER INFORMATION: /mod_base=OTHER
            / note="Nucleotide 10 has a tail which comprises
            a cholesterol moiety which has its A ring linked to
            the 3'- phosphate through a carbonyl group attached
            to the ring nitrogen of a moiety derived from 4-hydroxy-2- hydroxymethylpyrrolidine (see
formula 3)."

( x i ) SEQUENCE DESCRIPTION: SEQ ID NO:38:

GTGGGCCCAC                                                                                                                10

( 2 ) INFORMATION FOR SEQ ID NO:39:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i x ) FEATURE:
        ( A ) NAME/KEY: modified_base
        ( B ) LOCATION: 10
        ( D ) OTHER INFORMATION: /mod_base=OTHER
          / note="Nucleotide 10 has a tail which comprises a
          cholesterol moiety which has its A ring linked to
          the 3'- phosphate through a carbonyl group attached
          to the ring nitrogen of a moiety derived from
          4-hydroxy-2- hydroxymethylpyrrolidine (see
          formula 3)."

( x i ) SEQUENCE DESCRIPTION: SEQ ID NO:39:

ATATATATAT                                                                                                                10

( 2 ) INFORMATION FOR SEQ ID NO:40:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i x ) FEATURE:
        ( A ) NAME/KEY: modified_base
        ( B ) LOCATION: 10
        ( D ) OTHER INFORMATION: /mod_base=OTHER
          / note="Nucleotide 10 has a tail which comprises a
          cholesterol moiety which has its A ring linked to
          the 3'- phosphate through a carbonyl group attached
          to the ring nitrogen of a moiety derived from
          4-hydroxy-2- hydroxymethylpyrrolidine (see
          formula 3)."

( x i ) SEQUENCE DESCRIPTION: SEQ ID NO:40:

ACCACGTGGT                                                                                                                10

( 2 ) INFORMATION FOR SEQ ID NO:41:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i x ) FEATURE:
        ( A ) NAME/KEY: modified_base
        ( B ) LOCATION: 12
        ( D ) OTHER INFORMATION: /mod_base=OTHER
          / note="Nucleotide 12 has a tail which comprises a
          cholesterol moiety which has its A ring linked to
          the 3'- phosphate through a carbonyl group attached
          to the ring nitrogen of a moiety derived from
          4-hydroxy-2- hydroxymethylpyrrolidine (see
          formula 3)."

( x i ) SEQUENCE DESCRIPTION: SEQ ID NO:41:

CGCGAATTCG CG                                                                                                             12

( 2 ) INFORMATION FOR SEQ ID NO:42:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i x ) FEATURE:
        ( A ) NAME/KEY: modified_base
        ( B ) LOCATION: 14
        ( D ) OTHER INFORMATION: /mod_base=OTHER
        / note="Nucleotide 14 has a tail which comprises a cholesterol moiety which has its A ring linked to the 3'- phosphate through a carbonyl group attached to the ring nitrogen of a moiety derived from 4-hydroxy-2- hydroxymethylpyrrolidine (see formula 3)."

( x i ) SEQUENCE DESCRIPTION: SEQ ID NO:42:

AGACCACGTG GTCT         14

( 2 ) INFORMATION FOR SEQ ID NO:43:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i x ) FEATURE:
        ( A ) NAME/KEY: modified_base
        ( B ) LOCATION: 10
        ( D ) OTHER INFORMATION: /mod_base=OTHER
        / note="Nucleotide 10 has a tail which comprises a cholesterol moiety which has its A ring linked to the 3'- phosphate through a carbonyl group attached to the ring nitrogen of a moiety derived from 4-hydroxy-2- hydroxymethylpyrrolidine (see formula 3)."

( x i ) SEQUENCE DESCRIPTION: SEQ ID NO:43:

CACCCGTGTG         10

( 2 ) INFORMATION FOR SEQ ID NO:44:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i x ) FEATURE:
        ( A ) NAME/KEY: modified_base
        ( B ) LOCATION: 10
        ( D ) OTHER INFORMATION: /mod_base=OTHER
        / note="Nucleotide 10 has a tail which comprises a cholesterol moiety which has its A ring linked to the 3'- phosphate through a carbonyl group attached to the ring nitrogen of a moiety derived from 4-hydroxy-2- hydroxymethylpyrrolidine (see formula 3)."

( x i ) SEQUENCE DESCRIPTION: SEQ ID NO:44:

TTTATTATTT         10

( 2 ) INFORMATION FOR SEQ ID NO:45:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i x ) FEATURE:
    ( A ) NAME/KEY: modified_base
    ( B ) LOCATION: 10
    ( D ) OTHER INFORMATION: /mod_base=OTHER
        / note="Nucleotide 10 has a tail which comprises a
        cholesterol moiety which has its A ring linked to
        the 3'- phosphate through a carbonyl group attached
        to the ring nitrogen of a moiety derived from
        4-hydroxy-2- hydroxymethylpyrrolidine (see
        formula 3)."

( x i ) SEQUENCE DESCRIPTION: SEQ ID NO:45:

AAATAATAAA        10

( 2 ) INFORMATION FOR SEQ ID NO:46:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i x ) FEATURE:
        ( A ) NAME/KEY: modified_base
        ( B ) LOCATION: 10
        ( D ) OTHER INFORMATION: /mod_base=OTHER
            / note="Nucleotide 10 has a tail which comprises a
            cholesterol moiety which has its A ring linked to
            the 3'- phosphate through a carbonyl group attached
            to the ring nitrogen of a moiety derived from
            4-hydroxy-2- hydroxymethylpyrrolidine (see
            formula 3)."

( x i ) SEQUENCE DESCRIPTION: SEQ ID NO:46:

GCTATTATCG        10

( 2 ) INFORMATION FOR SEQ ID NO:47:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i x ) FEATURE:
        ( A ) NAME/KEY: modified_base
        ( B ) LOCATION: 10
        ( D ) OTHER INFORMATION: /mod_base=OTHER
            / note="Nucleotide 10 has a tail which comprises a
            cholesterol moiety which has its A ring linked to
            the 3'- phosphate through a carbonyl group attached
            to the ring nitrogen of a moiety derived from
            4-hydroxy-2- hydroxymethylpyrrolidine (see
            formula 3)."

( x i ) SEQUENCE DESCRIPTION: SEQ ID NO:47:

CGATAATAGC        10

( 2 ) INFORMATION FOR SEQ ID NO:48:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i x ) FEATURE:
        ( A ) NAME/KEY: modified_base
        ( B ) LOCATION: 12
        ( D ) OTHER INFORMATION: /mod_base=OTHER
            / note="Nucleotide 12 has a tail which comprises a
            cholesterol moiety which has its A ring linked to
            the 3'- phosphate through a carbonyl group attached
            to the ring nitrogen of a moiety derived from 4-hydroxy-2- hydroxymethylpyrrolidine (see formula 3)."

( x i ) SEQUENCE DESCRIPTION: SEQ ID NO:48:

CCACACGTGT GG                                                                                    12

( 2 ) INFORMATION FOR SEQ ID NO:49:

( i ) SEQUENCE CHARACTERISTICS:
    ( A ) LENGTH: 14 base pairs
    ( B ) TYPE: nucleic acid
    ( C ) STRANDEDNESS: single
    ( D ) TOPOLOGY: linear ( i x ) FEATURE:
    ( A ) NAME/KEY: modified_base
    ( B ) LOCATION: 14
    ( D ) OTHER INFORMATION: /mod_base=OTHER
          / note="Nucleotide 14 has a tail which comprises a
          cholesterol moiety which has its A ring linked to
          the 3'- phosphate through a carbonyl group attached
          to the ring nitrogen of a moiety derived from
          4-hydroxy-2- hydroxymethylpyrrolidine (see
          formula 3)."

( x i ) SEQUENCE DESCRIPTION: SEQ ID NO:49:

TCCACACGTG TGGA                                                                                   14

( 2 ) INFORMATION FOR SEQ ID NO:50:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i x ) FEATURE:
    ( A ) NAME/KEY: modified_base
    ( B ) LOCATION: 18
    ( D ) OTHER INFORMATION: /mod_base=OTHER
          / note="Nucleotide 18 has a tail which comprises a
          cholesterol moiety which has its A ring linked to
          the 3'- phosphate through a carbonyl group attached
          to the ring nitrogen of a moiety derived from
          4-hydroxy-2- hydroxymethylpyrrolidine (see
          formula 3)."

( x i ) SEQUENCE DESCRIPTION: SEQ ID NO:50:

ACTCCACACG TGTGGAGT                                                                               18

( 2 ) INFORMATION FOR SEQ ID NO:51:

( i ) SEQUENCE CHARACTERISTICS:
    ( A ) LENGTH: 10 base pairs
    ( B ) TYPE: nucleic acid
    ( C ) STRANDEDNESS: single
    ( D ) TOPOLOGY: linear ( i x ) FEATURE:
    ( A ) NAME/KEY: modified_base
    ( B ) LOCATION: 10
    ( D ) OTHER INFORMATION: /mod_base=OTHER
          / note="Nucleotide 10 has a tail which comprises a
          cholesterol moiety which has its A ring linked to
          the 3'- phosphate through a carbonyl group attached
          to the ring nitrogen of a moiety derived from
          4-hydroxy-2- hydroxymethylpyrrolidine (see
          formula 3)."

( x i ) SEQUENCE DESCRIPTION: SEQ ID NO:51:

TAGCATATGC                                                                                        10

( 2 ) INFORMATION FOR SEQ ID NO:52:

( i ) SEQUENCE CHARACTERISTICS:
    ( A ) LENGTH: 10 base pairs
    ( B ) TYPE: nucleic acid
    ( C ) STRANDEDNESS: single
    ( D ) TOPOLOGY: linear ( i x ) FEATURE:
    ( A ) NAME/KEY: modified_base
    ( B ) LOCATION: 10
    ( D ) OTHER INFORMATION: /mod_base=OTHER
     / note="Nucleotide 10 has a tail which comprises a
     cholesterol moiety which has its A ring linked to
     the 3'- phosphate through a carbonyl group attached
     to the ring nitrogen of a moiety derived from
     4-hydroxy-2- hydroxymethylpyrrolidine (see
     formula 3)."

( x i ) SEQUENCE DESCRIPTION: SEQ ID NO:52:

GCATATGCTA                                 10

( 2 ) INFORMATION FOR SEQ ID NO:53:

( i ) SEQUENCE CHARACTERISTICS:
    ( A ) LENGTH: 11 base pairs
    ( B ) TYPE: nucleic acid
    ( C ) STRANDEDNESS: single
    ( D ) TOPOLOGY: linear ( i x ) FEATURE:
    ( A ) NAME/KEY: modified_base
    ( B ) LOCATION: 11
    ( D ) OTHER INFORMATION: /mod_base=OTHER
     / note="Nucleotide 11 has a tail which comprises a
     cholesterol moiety which has its A ring linked to
     the 3'- phosphate through a carbonyl group attached
     to the ring nitrogen of a moiety derived from
     4-hydroxy-2- hydroxymethylpyrrolidine (see
     formula 3)."

( x i ) SEQUENCE DESCRIPTION: SEQ ID NO:53:

TAGCATATGC T                              11

( 2 ) INFORMATION FOR SEQ ID NO:54:

( i ) SEQUENCE CHARACTERISTICS:
    ( A ) LENGTH: 11 base pairs
    ( B ) TYPE: nucleic acid
    ( C ) STRANDEDNESS: single
    ( D ) TOPOLOGY: linear ( i x ) FEATURE:
    ( A ) NAME/KEY: modified_base
    ( B ) LOCATION: 11
    ( D ) OTHER INFORMATION: /mod_base=OTHER
     / note="Nucleotide 11 has a tail which comprises a
     cholesterol moiety which has its A ring linked to
     the 3'- phosphate through a carbonyl group attached
     to the ring nitrogen of a moiety derived from
     4-hydroxy-2- hydroxymethylpyrrolidine (see
     formula 3)."

( x i ) SEQUENCE DESCRIPTION: SEQ ID NO:54:

AGCATATGCT A                              11

( 2 ) INFORMATION FOR SEQ ID NO:55:

( i ) SEQUENCE CHARACTERISTICS:
    ( A ) LENGTH: 12 base pairs
    ( B ) TYPE: nucleic acid
    ( C ) STRANDEDNESS: single
    ( D ) TOPOLOGY: linear ( i x ) FEATURE:
    ( A ) NAME/KEY: modified_base
    ( B ) LOCATION: 12
    ( D ) OTHER INFORMATION: /mod_base=OTHER
        / note="Nucleotide 12 has a tail which comprises a
        cholesterol moiety which has its A ring linked to
        the 3'- phosphate through a carbonyl group attached
        to the ring nitrogen of a moiety derived from
        4-hydroxy-2- hydroxymethylpyrrolidine (see
        formula 3)."

( x i ) SEQUENCE DESCRIPTION: SEQ ID NO:55:

ATAGCATATG CT            12

( 2 ) INFORMATION FOR SEQ ID NO:56:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i x ) FEATURE:
        ( A ) NAME/KEY: modified_base
        ( B ) LOCATION: 12
        ( D ) OTHER INFORMATION: /mod_base=OTHER
            / note="Nucleotide 12 has a tail which comprises a
            cholesterol moiety which has its A ring linked to
            the 3'- phosphate through a carbonyl group attached
            to the ring nitrogen of a moiety derived from
            4-hydroxy-2- hydroxymethylpyrrolidine (see
            formula 3)."

( x i ) SEQUENCE DESCRIPTION: SEQ ID NO:56:

AGCATATGCT AT            12

( 2 ) INFORMATION FOR SEQ ID NO:57:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i x ) FEATURE:
        ( A ) NAME/KEY: modified_base
        ( B ) LOCATION: 14
        ( D ) OTHER INFORMATION: /mod_base=OTHER
            / note="Nucleotide 14 has a tail which comprises a
            cholesterol moiety which has its A ring linked to
            the 3'- phosphate through a carbonyl group attached
            to the ring nitrogen of a moiety derived from
            4-hydroxy-2- hydroxymethylpyrrolidine (see
            formula 3)."

( x i ) SEQUENCE DESCRIPTION: SEQ ID NO:57:

GATAGCATAT GCTA          14

( 2 ) INFORMATION FOR SEQ ID NO:58:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i x ) FEATURE:
        ( A ) NAME/KEY: modified_base
        ( B ) LOCATION: 14
        ( D ) OTHER INFORMATION: /mod_base=OTHER
            / note="Nucleotide 14 has a tail which comprises a
            cholesterol moiety which has its A ring linked to
            the 3'- phosphate through a carbonyl group attached
            to the ring nitrogen of a moiety derived from 4-hydroxy-2- hydroxymethylpyrrolidine (see
                formula 3)."

( x i ) SEQUENCE DESCRIPTION: SEQ ID NO:58:

TAGCATATGC TATC                                                                                 14

( 2 ) INFORMATION FOR SEQ ID NO:59:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i x ) FEATURE:
        ( A ) NAME/KEY: modified_base
        ( B ) LOCATION: 18
        ( D ) OTHER INFORMATION: /mod_base=OTHER
                / note="Nucleotide 18 has a tail which comprises a
                cholesterol moiety which has its A ring linked to
                the 3'- phosphate through a carbonyl group attached
                to the ring nitrogen of a moiety derived from
                4-hydroxy-2- hydroxymethylpyrrolidine (see
                formula 3)."

( x i ) SEQUENCE DESCRIPTION: SEQ ID NO:59:

AGGATAGCAT ATGCTACC                                                                             18

( 2 ) INFORMATION FOR SEQ ID NO:60:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i x ) FEATURE:
        ( A ) NAME/KEY: modified_base
        ( B ) LOCATION: 18
        ( D ) OTHER INFORMATION: /mod_base=OTHER
                / note="Nucleotide 18 has a tail which comprises a
                cholesterol moiety which has its A ring linked to
                the 3'- phosphate through a carbonyl group attached
                to the ring nitrogen of a moiety derived from
                4-hydroxy-2- hydroxymethylpyrrolidine (see
                formula 3)."

( x i ) SEQUENCE DESCRIPTION: SEQ ID NO:60:

GGTAGCATAT GCTATCCT                                                                             18

( 2 ) INFORMATION FOR SEQ ID NO:61:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i x ) FEATURE:
        ( A ) NAME/KEY: modified_base
        ( B ) LOCATION: 10
        ( D ) OTHER INFORMATION: /mod_base=OTHER
                / note="Nucleotide 10 has a tail which comprises a
                cholesterol moiety which has its A ring linked to
                the 3'- phosphate through a carbonyl group attached
                to the ring nitrogen of a moiety derived from
                4-hydroxy-2- hydroxymethylpyrrolidine (see
                formula 3)."

( x i ) SEQUENCE DESCRIPTION: SEQ ID NO:61:

ACCACGTGGT                                                                                      10

(2) INFORMATION FOR SEQ ID NO:62:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ix) FEATURE:
        (A) NAME/KEY: modified_base
        (B) LOCATION: 14
        (D) OTHER INFORMATION: /mod_base=OTHER
            / note="Nucleotide 14 has a tail which comprises a
            cholesterol moiety which has its A ring linked to
            the 3'- phosphate through a carbonyl group attached
            to the ring nitrogen of a moiety derived from
            4-hydroxy-2- hydroxymethylpyrrolidine (see
            formula 3)."

(xi) SEQUENCE DESCRIPTION: SEQ ID NO:62:

AGACCACGTG GTCT                                        14

(2) INFORMATION FOR SEQ ID NO:63:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ix) FEATURE:
        (A) NAME/KEY: modified_base
        (B) LOCATION: 18
        (D) OTHER INFORMATION: /mod_base=OTHER
            / note="Nucleotide 18 has a tail which comprises a
            cholesterol moiety which has its A ring linked to
            the 3'- phosphate through a carbonyl group attached
            to the ring nitrogen of a moiety derived from
            4-hydroxy-2- hydroxymethylpyrrolidine (see
            formula 3)."

(xi) SEQUENCE DESCRIPTION: SEQ ID NO:63:

GCAGACCACG TGGTCTGC                                  18

(2) INFORMATION FOR SEQ ID NO:64:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ix) FEATURE:
        (A) NAME/KEY: modified_base
        (B) LOCATION: 11
        (D) OTHER INFORMATION: /mod_base=OTHER
            / note="Position 11 is not a nucleotide. It is
            -(OCH2CH2)3-O- which joins the nucleotide at
            position 10 with the nucleotide at position 12."

(ix) FEATURE:
        (A) NAME/KEY: modified_base
        (B) LOCATION: 21
        (D) OTHER INFORMATION: /mod_base=OTHER
            / note="Nucleotide 21 has a tail which comprises
            a cholesterol moiety which has its A ring linked to
            the 3'- phosphate through a carbonyl group attached
            to the ring nitrogen of a moiety derived from
            4-hydroxy-2- hydroxymethylpyrrolidine (see formula 3)."

(xi) SEQUENCE DESCRIPTION: SEQ ID NO:64:

CACCCGGGTG NCACCCGGGT G                            21

(2) INFORMATION FOR SEQ ID NO:65:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i x ) FEATURE:
    ( A ) NAME/KEY: modified_base
    ( B ) LOCATION: 11
    ( D ) OTHER INFORMATION: /mod_base=OTHER
        / note="Position 11 is not a nucleotide. It is
        - ( O C H 2 C H 2 )3-O- which links the nucleotide at
        position 10 with the nucleotide at position 12."

( i x ) FEATURE:
    ( A ) NAME/KEY: modified_base
    ( B ) LOCATION: 21
    ( D ) OTHER INFORMATION: /mod_base=OTHER
        / note="Nucleotide 21 has a tail which comprises
        a cholesterol moiety which has its A ring linked to
        the 3'- phosphate through a carbonyl group attached
        to the ring nitrogen of a moiety derived from
        4-hydroxy-2- hydroxymethylpyrrolidine (see formula 3)."

( x i ) SEQUENCE DESCRIPTION: SEQ ID NO:65:

CACACGTGTG  NCACACGTGT  G                                    2 1

( 2 ) INFORMATION FOR SEQ ID NO:66:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i x ) FEATURE:
    ( A ) NAME/KEY: modified_base
    ( B ) LOCATION: 24
    ( D ) OTHER INFORMATION: /mod_base=OTHER
        / note="Nucleotide 24 has a tail which comprises
        a cholesterol moiety which has its A ring linked to
        the 3'- phosphate through a carbonyl group attached
        to the ring nitrogen of a moiety derived from
        4-hydroxy-2- hydroxymethylpyrrolidine (see formula 3)."

( x i ) SEQUENCE DESCRIPTION: SEQ ID NO:66:

CACACGTGTG  GAAACACACG  TGTG                                2 4

( 2 ) INFORMATION FOR SEQ ID NO:67:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i x ) FEATURE:
    ( A ) NAME/KEY: modified_base
    ( B ) LOCATION: 24
    ( D ) OTHER INFORMATION: /mod_base=OTHER
        / note="Nucleotide 24 has a tail which comprises
        a cholesterol moiety which has its A ring linked to
        the 3'- phosphate through a carbonyl group attached
        to the ring nitrogen of a moiety derived from
        4-hydroxy-2- hydroxymethylpyrrolidine (see formula 3)."

( x i ) SEQUENCE DESCRIPTION: SEQ ID NO:67:

CACACGTGTG  TTTTCACACG  TGTG                                2 4

( 2 ) INFORMATION FOR SEQ ID NO:68:

( i ) SEQUENCE CHARACTERISTICS:
    ( A ) LENGTH: 25 base pairs (B) TYPE: nucleic acid
        (C) STRANDEDNESS: single
        (D) TOPOLOGY: linear (ix) FEATURE:
        (A) NAME/KEY: modified_base
        (B) LOCATION: 13
        (D) OTHER INFORMATION: /mod_base=OTHER
            /note="Position 13 is not a nucleotide. It is
            4-hydroxy-2- hydroxymethylpyrrolidine with a
            carbonyl attached to the N and cholesterol
            attached to the C of the carbonyl via the O of
            the A ring. This connects the nucleotide at
            position 12 to the nucleotide at position 14 (see
            figure 14)."

(ix) FEATURE:
        (A) NAME/KEY: modified_base
        (B) LOCATION: 25
        (D) OTHER INFORMATION: /mod_base=OTHER
            /note="Nucleotide 25 has a tail which comprises
            a cholesterol moiety which has its A ring linked to
            the 3'- phosphate through a carbonyl group attached
            to the ring nitrogen of a moiety derived from
            4-hydroxy-2- hydroxymethylpyrrolidine (see formula 3)."

(xi) SEQUENCE DESCRIPTION: SEQ ID NO:68:

CACACGTGTG TTNTTCACAC GTGTG                                           25

(2) INFORMATION FOR SEQ ID NO:69:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ix) FEATURE:
        (A) NAME/KEY: modified_base
        (B) LOCATION: 20
        (D) OTHER INFORMATION: /mod_base=OTHER
            /note="Nucleotide 20 has a tail which comprises
            a cholesterol moiety which has its A ring linked to
            the 3'- phosphate through a carbonyl group attached
            to the ring nitrogen of a moiety derived from
            4-hydroxy-2- hydroxymethylpyrrolidine (see formula 3)."

(xi) SEQUENCE DESCRIPTION: SEQ ID NO:69:

ACACGTGTTT TTACACGTGT                                                 20

(2) INFORMATION FOR SEQ ID NO:70:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ix) FEATURE:
        (A) NAME/KEY: modified_base
        (B) LOCATION: 16
        (D) OTHER INFORMATION: /mod_base=OTHER
            /note="Nucleotide 16 has a tail which comprises
            a cholesterol moiety which has its A ring linked to
            the 3'- phosphate through a carbonyl group attached
            to the ring nitrogen of a moiety derived from
            4-hydroxy-2- hydroxymethylpyrrolidine (see formula 3)."

(xi) SEQUENCE DESCRIPTION: SEQ ID NO:70:

CACGTGTTTT CACGTG                                                     16

What is claimed is:

1. A duplex of two strands of oligonucleotides each of which has the formula

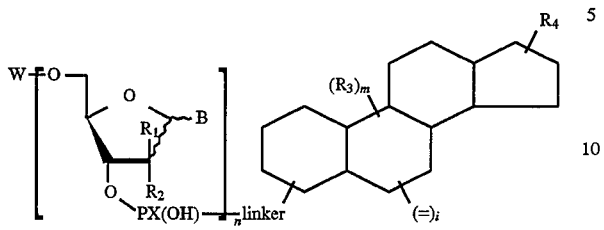

wherein each of B independently is a nucleotide base residue;

the wavy line between the sugar and the base B represents a glycosidic bond of either α or of β configuration;

X is S or O, with the proviso that there are no more than 3 X=S groups in each oligonucleotide;

$R_1$ is H, OH, or F;

$R_2$ is H, or F;

W is H or YO(OH)XP-;

Y is H, alkyl of 1–20 carbons, branched chain alkyl or cycloalkyl of 3 to 25 carbons, $(CH_2)_sOH$, $(CH_2)_sNH_2$, hydroxy branched chain alkyl or hydroxy cycloalkyl of 3–25 carbons, amino branched chain alkyl of 3 to 25 carbons or amino cycloalkyl of 3 to 25 carbons, or a lipophilic group which may be connected to the phosphate residue with an appendant connecting group of 1 to 10 atom length, s is an integer between 2–25;

n is an integer having a value between 8 and 18;

the linker is a group of 0 to 12 atom length covalently linking the A ring of the steroid skeleton to the 3'-phosphate end of the oligonucleotide;

$R_3$ is H, $C_1$–$C_6$ alkyl, or $C_2$–$C_6$ alkenyl and is attached to the A, B or C ring of the steroid skeleton, m is an integer having the values 0 to 4, i is an integer having the values 0 to 4, and $R_4$ is H or a $C_1$ to $C_{15}$ alkyl group, or a $C_2$ to $C_{15}$ alkenyl group having 1 to 3 double bonds and the $R_4$ group is attached to the D ring of the steroid skeleton;

the nucleotide base residues B are selected such that the two strands of the oligonucleotides are substantially complementary to one another for Watson Crick type base pairing and the two strands form a stable duplex in aqueous solution at physiological temperature.

2. The duplex of claim 1 wherein the two strands are identical with one another.

3. The duplex of claim 2 wherein the melting temperature of the duplex of the oligonucleotides is above approximately 25° C., as determined in an approximately 3.0 μmolar concentration of the duplex.

4. The duplex of claim 3 wherein $R_1$ and $R_2$ are both hydrogen and the wavy line represents glycosidic bonds of β configuration.

5. The duplex of claim 4 wherein W is hydrogen.

6. The duplex of claim 4 wherein the linker represents the group of the formula

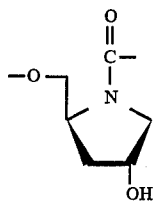

7. The duplex of claim 4 wherein the linker is attached to the secondary hydroxyl group of cholesterol.

8. The duplex of claim 4 wherein the strand consists of 8 to 12 nucleotide units.

9. The duplex of claim 1 wherein the two strands are not identical with one another.

10. The duplex of claim 9 wherein the melting temperature of the duplex is above approximately 25° C., as determined in an approximately 3.0 μmolar concentration of the duplex.

11. The duplex of claim 10 wherein $R_1$ and $R_2$ are both hydrogen and the wavy line represents glycosidic bonds of β configuration.

12. The duplex of claim 11 wherein W is hydrogen.

13. The duplex of claim 11 wherein the linker represents the group of the formula

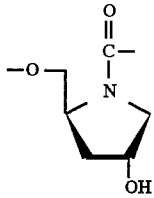

14. The duplex of claim 11 wherein the linker is attached to the secondary hydroxyl group of cholesterol.

15. The duplex of claim 11 wherein each strand consists of 8 to 14 nucleotide units.

16. A duplex of two strands of oligonucleotides each of which has the formula

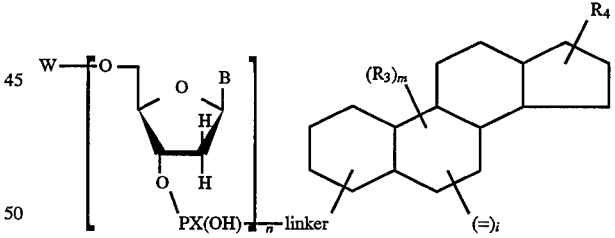

wherein each of B independently is a major naturally occurring nucleotide base residue selected from the group consisting of 1-N-uracil, 1-N-thymine, 1-N-cytosine, 9-N-adenine and 9-N-guanine residues;

X is S or O, with the proviso that there are no more than 3 X=S groups in each oligonucleotide;

W is H or YO(OH)XP-;

Y is H, alkyl of 1–20 carbons, branched chain alkyl or cycloalkyl of 3 to 25 carbons, $(CH_2)_sOH$, $(CH_2)_sNH2$, hydroxy branched chain alkyl or hydroxy cycloalkyl of 3–25 carbons, amino branched chain alkyl of 3 to 25 carbons or amino cycloalkyl of 3 to 25 carbons, or a lipophilic group which may be connected to the phosphate residue with an appendant connecting group of 1 to 10 atom length, s is an integer between 2–25;

n is an integer having a value between 8 and 18;

the linker is a group of 0 to 12 atom length covalently linking the A ring of the steroid skeleton to the 3'-phosphate end of the oligonucleotide;

$R_3$ is H, $C_1$-$C_6$ alkyl, or $C_2$-$C_6$ alkenyl and is attached to the A, B or C ring of the steroid skeleton, m is an integer having the values 0 to 4, i is an integer having the values 0 to 4, and $R_4$ is H or a $C_1$ to $C_{15}$ alkyl group, or a $C_2$ to $C_{15}$ alkenyl group having 1 to 3 double bonds and the $R_4$ group is attached to the D ring of the steroid skeleton;

the nucleotide base residues B are selected such that the two strands of the oligonucleotides are substantially complementary to one another for Watson Crick type base pairing and the two strands form a substantially stable duplex in aqueous solution at 25° C. or still higher temperatures.

17. The duplex of claim 16 wherein the linker is selected from the structures

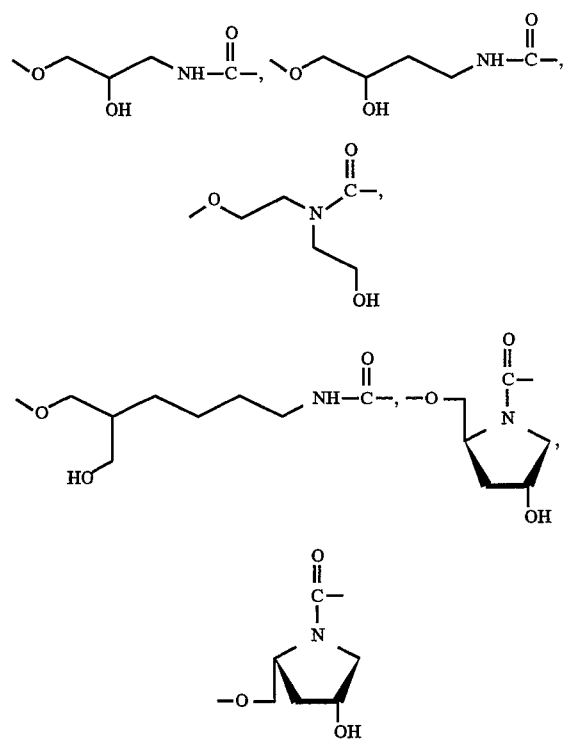

18. The duplex of claim 16 where the linker is selected from the structures

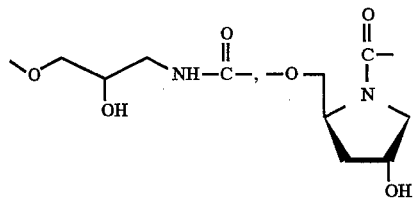

19. The duplex of claim 18 wherein the linker is attached via the carbonyl to the secondary hydroxyl group of a cholesterol moiety.

20. The duplex of claim 19 wherein each strand consists of 8 to 14 nucleotide units.

21. The duplex of claim 20 wherein the two strands of the combination are identical and self-complementary, and have the sequence selected from the sequences CACACGGGTG (SEQUENCE ID NO: 5), GACACACGGGTGAT (SEQUENCE ID NO: 1), CACACGGGTGAT (SEQUENCE ID NO: 3), CACACGGGTGA (SEQUENCE ID NO: 4), CACACCGGTG fSEQUENCE ID NO: 18), CACCCGGGTG (SEQUENCE ID NO: 26), CACACGAGTG (SEQUENCE ID NO: 32), CACACGCGTG (SEOqENCE ID NO: 33), and CACACGTGTG (SEOUENCE ID NO: 34).

22. The duplex of claim 21 wherein the 3'-phosphate group of each strand is connected to the group of the formula

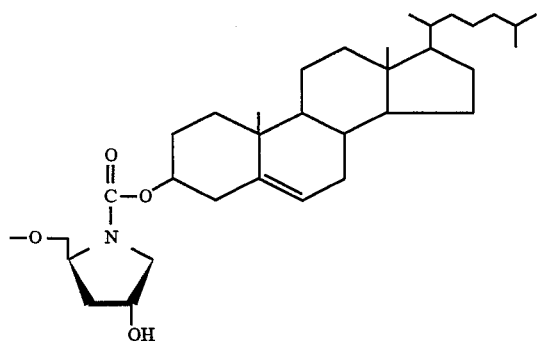

23. The duplex of claim 20 wherein the two strands of the combination are different but substantially complementary to one another, and wherein one of the strands has the sequence selected from the sequences CACACGGGTG fSEQUENCE ID NO: 5), GATAGCATATGCTA (SEQUENCE ID NO: 57), and GCTATTATCG (SEQUENCE ID NO: 46).

24. The duplex of claim 23 wherein the 3'-phosphate group of each strand is connected to the group of the formula

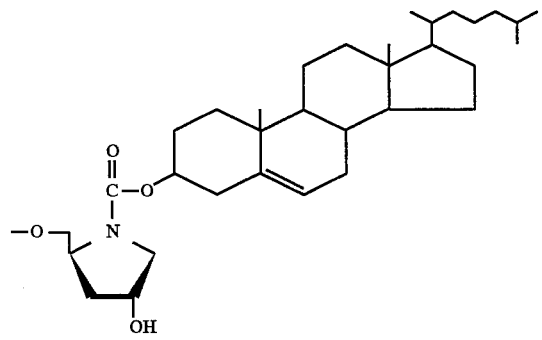

25. The duplex of claim 22 wherein X in each nucleotide unit is O.

26. The duplex of claim 25 wherein W is H.

27. The duplex of claim 24 wherein X in each nucleotide unit is O.

28. The duplex of claim 27 wherein W is H.

29. An oligonucleotide which has the formula

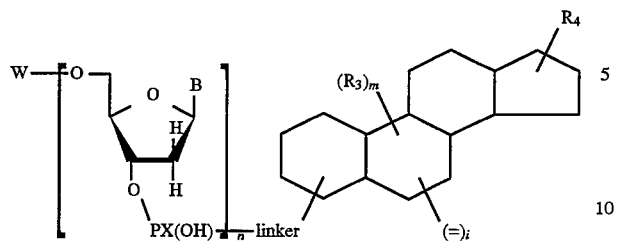

wherein each of B independently is a major naturally occurring nucleotide base residue selected from the group consisting of 1-N-uracil, 1-N-thymine, 1-N-cytosine, 9-N-adenine and 9-N-guanine residues;

X is S or O, with the proviso that there are no more than 3 X=S groups in the oligonucleotide;

W is H or YO(OH)XP-;

Y is H, alkyl of 1-20 carbons, branched chain alkyl or cycloalkyl of 3 to 25 carbons, $(CH_2)_sOH$, $(CH_2)_sNH2$, hydroxy branched chain alkyl or hydroxy cycloalkyl of 3-25 carbons, amino branched chain alkyl of 3 to 25 carbons or amino cycloalkyl of 3 to 25 carbons, or a lipophilic group which may be connected to the phosphate residue with an appendant connecting group of 1 to 10 atom length, s is an integer between 2-25;

n is an integer having a value between 8 and 14;

the linker is a group of 0 to 12 atom length covalently linking the A ring of the steroid skeleton to the 3'-phosphate end of the oligonucleotide;

$R_3$ is H, $C_1$-$C_6$ alkyl, or $C_2$-$C_6$ alkenyl and is attached to the A, B or C ring of the steroid skeleton, m is an integer having the values 0 to 4, i is an integer having the values 0 to 4, and $R_4$ is H or a $C_1$ to $C_{15}$ alkyl group, or a $C_2$ to $C_{15}$ alkenyl group having 1 to 3 double bonds and the $R_4$ group is attached to the D ring of the steroid skeleton;

the nucleotide base residues B are selected such that the oligonucleotide is substantially self-complementary to itself to form a duplex by Watson Crick type base pairing, the sequence of the oligonucleotide being selected from the sequences CACACGGGTG (SEQUENCE ID NO: 5), GACACACGGGTGAT (SEQUENCE ID NO: 1)., CACACGGGTGAT (SEQUENCE ID NO: 3), CACACGGGTGA (SEQUENCE ID NO: 4), CACACCGGTG (SEQUENCE ID NO: 18), CACCCGGGTG (SEQUENCE ID NO: 26), CACACGAGTG (SEQUENCE ID NO: 32), CACACGCGTG (SEQUENCE ID NO: 33), and CACACGTGTG (SEQUENCE ID NO: 34).

30. The oligonucleotide of claim 29 wherein W is H, X in each nucleotide unit is O, and where the linker is selected from the structures

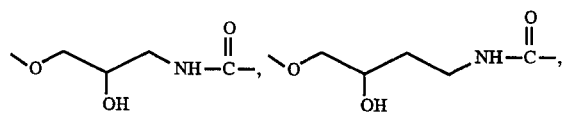

-continued

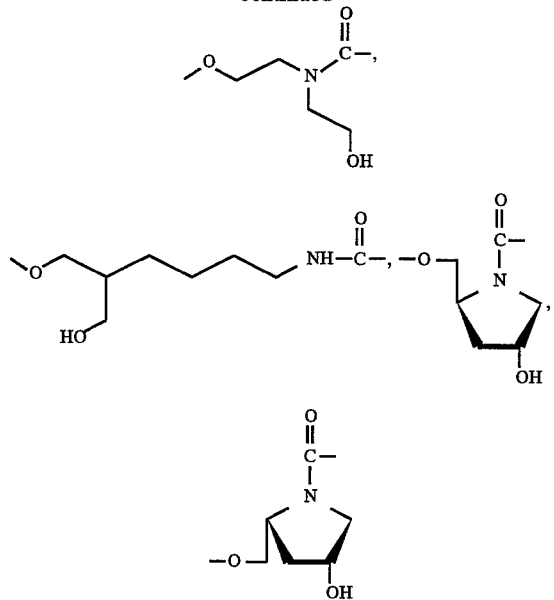

31. A duplex of two strands of oligonucleotides each of which has the formula

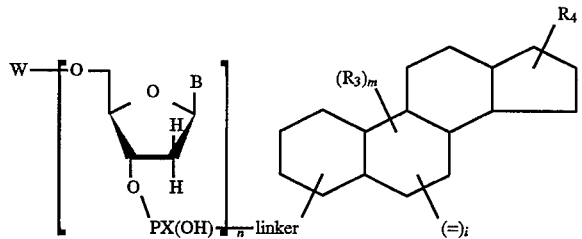

wherein each of B independently is a major naturally occurring nucleotide base residue selected from the group consisting of 1-N-uracil, 1-N-thymine, 1-N-cytosine, 9-N-adenine and 9-N-guanine residues;

X is S or O, with the proviso that there are no more than 3 X=S groups in each oligonucleotide;

W is H or YO(OH)XP-;

Y is H, alkyl of 1-20 carbons, branched chain alkyl or cycloalkyl of 3 to 25 carbons, $(CH_2)_sOH$, $(CH_2)_sNH2$, hydroxy branched chain alkyl or hydroxy cycloalkyl of 3-25 carbons, amino branched chain alkyl of 3 to 25 carbons or amino cycloalkyl of 3 to 25 carbons, or a lipophilic group which may be connected to the phosphate residue with an appendant connecting group of 1 to 10 atom length, s is an integer between 2-25;

n is an integer having a value between 8 and 14;

the linker is a group of 0 to 12 atom length covalently linking the steroid skeleton the 3'-phosphate end of the oligonucleotide;

$R_3$ is H, $C_1$-$C_6$ alkyl, or $C_2$-$C_6$ alkenyl and is attached to the A, B or C ring of the steroid skeleton, m is an integer having the values 0 to 4, i is an integer having the values 0 to 4, and $R_4$ is H or a $C_1$ to $C_{15}$ alkyl group, or a $C_2$ to $C_{15}$ alkenyl group having 1 to 3 double bonds and the $R_4$ group is attached to the D ring of the steroid skeleton;

the nucleotide base residues B are selected such that the two strands of the oligonucleitides are substantially complementary to one another for Watson Crick type base pairing and wherein one of the strands has the sequence selected from the sequences CACACGGGTG (SEQUENCE ID NO: 5), GATAG-CATATGCTA (SEQUENCE ID NO: 57), and GCTAT-TATCG (SEQUENCE ID NO: 46).
32. The duplex of claim 31 wherein W is H, X in each nucleotide unit is O, and where the linker is selected from the structures
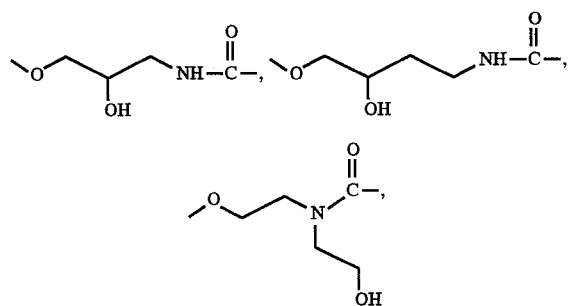
-continued
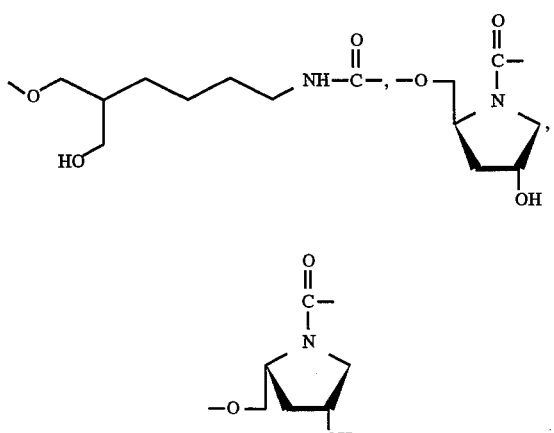
* * * * *

UNITED STATES PATENT AND TRADEMARK OFFICE
CERTIFICATE OF CORRECTION

PATENT NO. : 5,646,126

DATED : July 8, 1997

INVENTOR(S) : Cheng et al.

It is certified that error appears in the above-indentified patent and that said Letters Patent is hereby corrected as shown below:

Column 2, line 51, "asteroid" should be --a steroid--.

Column 3, line 22, "e.q." should be --e.g.--.

Column 6, line 63, "10 mer" should be --10mer--.

Column 6, line 66, "14 mer" should be --14mer--.

Column 7, line 1, "10 mer" should be --10mer--.

Column 7, line 7, "10 mer" should be --10mer--.

Column 7, line 17, "10 mer" should be --10mer--.

Column 7, line 18, "14 mer" should be --14mer--.

Column 7, line 23, "10 mer" should be --10mer--.

Column 12, line 6, "e.q." should be --e.g.--.

Column 12, line 7, "e, g." should be --e.g.--.

Column 64, line 61, "$(CH_2)_sNH2$" should be --$(CH_2)_sNH_2$--.

Column 66, line 10, "fSEQUENCE" should be --(SEQUENCE--.

Column 66, line 13, "(SEOqUENCE" should be --(SEQUENCE--.

Column 66, line 36, "fSEQUENCE" should be --(SEQUENCE--.

Column 67, line 22, "$(CH_2)_sNH2$" should be --$(CH_2)_sNH_2$--.

Column 67, line 49, after "(SEQUENCE ID NO: 1)", delete ".".

UNITED STATES PATENT AND TRADEMARK OFFICE
CERTIFICATE OF CORRECTION

PATENT NO. : 5,646,126
DATED : July 8, 1997
INVENTOR(S) : Cheng, et al

It is certified that error appears in the above-identified patent and that said Letters Patent is hereby corrected as shown below:

Column 68, line 48, "$(CH_2)_sNH2$" should be -- $(CH_2)_sNH_2$ --.

Signed and Sealed this

Twenty-sixth Day of May, 1998

Attest:

BRUCE LEHMAN

Attesting Officer

Commissioner of Patents and Trademarks